United States Patent
Yontz et al.

(10) Patent No.: US 9,549,886 B2
(45) Date of Patent: *Jan. 24, 2017

(54) PERSONAL CARE FORMULATIONS CONTAINING ALKYL KETAL ESTERS AND METHODS OF MANUFACTURE

(71) Applicant: SEGETIS, INC., Golden Valley, MN (US)

(72) Inventors: Dorie J. Yontz, Bloomington, MN (US); Lee Richard Rieth, Plymouth, MN (US); Nicholas Morante, Holbrook, NY (US); Irwin Palefsky, Fairfield, NJ (US)

(73) Assignee: GFBIOCHEMICALS LIMITED, Valletta (MT)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,989

(22) Filed: Nov. 7, 2014

(65) Prior Publication Data

US 2015/0064124 A1    Mar. 5, 2015

Related U.S. Application Data

(62) Division of application No. 13/104,570, filed on May 10, 2011, now abandoned.

(60) Provisional application No. 61/332,982, filed on May 10, 2010, provisional application No. 61/332,978, filed on May 10, 2010.

(51) Int. Cl.

| | | |
|---|---|---|
| A61K 8/49 | (2006.01) | |
| A61Q 15/00 | (2006.01) | |
| A61K 8/35 | (2006.01) | |
| A61K 8/368 | (2006.01) | |
| A61Q 9/04 | (2006.01) | |
| A61K 8/34 | (2006.01) | |
| A61Q 5/10 | (2006.01) | |
| A61Q 1/02 | (2006.01) | |
| A61K 8/25 | (2006.01) | |
| A61K 8/29 | (2006.01) | |
| A61K 8/31 | (2006.01) | |
| A61K 8/92 | (2006.01) | |
| A61Q 1/04 | (2006.01) | |
| A61Q 1/10 | (2006.01) | |
| A61Q 1/12 | (2006.01) | |
| A61Q 3/00 | (2006.01) | |
| A61Q 1/06 | (2006.01) | |
| C09D 7/12 | (2006.01) | |
| A01N 25/00 | (2006.01) | |
| A61K 8/97 | (2006.01) | |
| A61K 47/22 | (2006.01) | |
| A61Q 17/04 | (2006.01) | |
| C08K 5/156 | (2006.01) | |

(52) U.S. Cl.
CPC .............. *A61K 8/498* (2013.01); *A01N 25/00* (2013.01); *A61K 8/25* (2013.01); *A61K 8/29* (2013.01); *A61K 8/31* (2013.01); *A61K 8/34* (2013.01); *A61K 8/35* (2013.01); *A61K 8/368* (2013.01); *A61K 8/4953* (2013.01); *A61K 8/4973* (2013.01); *A61K 8/922* (2013.01); *A61K 8/925* (2013.01); *A61K 8/927* (2013.01); *A61K 8/97* (2013.01); *A61K 47/22* (2013.01); *A61Q 1/02* (2013.01); *A61Q 1/04* (2013.01); *A61Q 1/06* (2013.01); *A61Q 1/10* (2013.01); *A61Q 1/12* (2013.01); *A61Q 3/00* (2013.01); *A61Q 5/10* (2013.01); *A61Q 9/04* (2013.01); *A61Q 15/00* (2013.01); *A61Q 17/04* (2013.01); *C09D 7/1233* (2013.01); *A61K 2800/49* (2013.01); *C08K 5/156* (2013.01)

(58) Field of Classification Search
CPC ............ A61K 47/22; A61K 8/31; A61K 8/35; A61K 8/368; A61K 8/4953; A61K 8/4973; C08K 5/156

See application file for complete search history.

(56) References Cited

U.S. PATENT DOCUMENTS

| | | |
|---|---|---|
| 1,934,309 A | 10/1927 | Hoover |
| 2,004,115 A | 6/1935 | Izard et al. |
| 2,008,720 A | 7/1935 | Lawson |
| 2,260,261 A | 10/1941 | Morey et al. |
| 2,654,723 A | 10/1953 | Greene |
| 2,556,135 A | 6/1954 | Croxall et al. |
| 2,985,536 A | 5/1961 | Stein et al. |
| 3,201,420 A | 8/1965 | Fuzesi et al. |

(Continued)

FOREIGN PATENT DOCUMENTS

| | | |
|---|---|---|
| CA | 1000285 | 11/1976 |
| DE | 10036423 A1 | 3/2001 |

(Continued)

OTHER PUBLICATIONS

European Search Report for European Application No. 11781170.3, Report Date Dec. 17, 2014, 12 pages.

(Continued)

*Primary Examiner* — Anna Falkowitz
(74) *Attorney, Agent, or Firm* — Cantor Colburn LLP

(57) ABSTRACT

Personal care formulations containing alkyl ketal esters having the structure

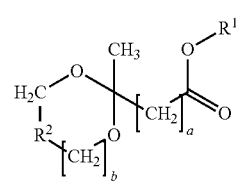

wherein a is 0 or an integer of 1 to 12; b is 0 or 1; $R^2$ is a divalent $C_{1-8}$ group optionally substituted with up to 5 hydroxyl groups; and $R^1$ is $C_{1-6}$ alkyl.

31 Claims, No Drawings

(56) References Cited

U.S. PATENT DOCUMENTS

| | | |
|---|---|---|
| 3,658,789 A | 4/1972 | Fried |
| 3,821,363 A | 6/1974 | Black et al. |
| 3,855,248 A | 12/1974 | Lannert et al. |
| 3,895,104 A | 7/1975 | Karg |
| 4,005,210 A | 1/1977 | Gubernick |
| 4,153,064 A | 5/1979 | Sawada et al. |
| 4,172,122 A | 10/1979 | Kubik et al. |
| 4,193,989 A | 3/1980 | Teng et al. |
| 4,387,089 A | 6/1983 | De Polo |
| 4,460,767 A | 7/1984 | Matsumura et al. |
| 4,465,866 A | 8/1984 | Takaishi et al. |
| 4,562,067 A | 12/1985 | Hopp |
| 4,663,157 A | 5/1987 | Brock |
| 4,668,505 A | 5/1987 | Grollier et al. |
| 4,710,373 A | 12/1987 | Nakamura et al. |
| 4,724,240 A | 2/1988 | Abrutym |
| 4,731,242 A | 3/1988 | Palinczar |
| 4,737,426 A | 4/1988 | Roth |
| 4,792,411 A | 12/1988 | Walsh |
| 4,806,448 A | 2/1989 | Roth |
| 4,847,072 A | 7/1989 | Bissett et al. |
| 4,897,497 A | 1/1990 | Fitzpatrick |
| 5,013,543 A | 5/1991 | Mercado et al. |
| 5,093,111 A | 3/1992 | Baker et al. |
| 5,116,604 A | 5/1992 | Fogel et al. |
| 5,145,669 A | 9/1992 | Kwak et al. |
| 5,204,090 A | 4/1993 | Han |
| 5,208,011 A | 5/1993 | Vaughan |
| 5,302,376 A | 4/1994 | Forestier et al. |
| 5,455,025 A | 10/1995 | Pereira et al. |
| 5,505,935 A | 4/1996 | Guerrero et al. |
| 5,573,755 A | 11/1996 | Franklin et al. |
| 5,605,680 A | 2/1997 | Deflandre et al. |
| 5,608,105 A | 3/1997 | Fitzpatrick |
| 5,620,682 A | 4/1997 | Fogel |
| 5,653,965 A | 8/1997 | Narayanan et al. |
| 5,667,765 A | 9/1997 | Hansenne et al. |
| 5,672,337 A | 9/1997 | Ascione et al. |
| 5,700,522 A | 12/1997 | Nonweiler et al. |
| 5,705,087 A | 1/1998 | Mushrush et al. |
| 5,725,844 A | 3/1998 | Gers-Barlag et al. |
| 5,783,174 A | 7/1998 | Deckner |
| 5,859,263 A | 1/1999 | Ghorpade et al. |
| 5,917,059 A | 6/1999 | Bruchmann et al. |
| 5,998,092 A | 12/1999 | McCulloch et al. |
| 6,036,925 A | 3/2000 | Adams et al. |
| 6,048,517 A | 4/2000 | Kaplan |
| 6,071,501 A | 6/2000 | Robinson |
| 6,130,195 A | 10/2000 | Doyel et al. |
| 6,238,650 B1 | 5/2001 | Lapidot et al. |
| 6,239,087 B1 | 5/2001 | Mao et al. |
| 6,306,249 B1 | 10/2001 | Galante et al. |
| 6,312,672 B1 | 11/2001 | Coolbaugh et al. |
| 6,321,465 B1 | 11/2001 | Bonk et al. |
| 6,372,791 B1 | 4/2002 | Shapiro et al. |
| 6,395,269 B1 | 5/2002 | Fuller et al. |
| 6,395,810 B1 | 5/2002 | Luitjes et al. |
| 6,403,109 B1 | 6/2002 | Stora |
| 6,423,480 B2 | 7/2002 | Ichiki |
| 6,444,195 B1 | 9/2002 | Cole et al. |
| 6,451,223 B1 | 9/2002 | Jeon |
| 6,485,713 B1 | 11/2002 | Bonda et al. |
| 6,627,181 B1 | 9/2003 | Busch, Jr. et al. |
| 6,703,478 B2 | 3/2004 | Nakane et al. |
| 6,749,998 B2 | 6/2004 | Schwartzkopf et al. |
| 6,844,302 B1 | 1/2005 | Boden et al. |
| 7,038,046 B2 | 5/2006 | Wagner |
| 7,094,395 B1 | 8/2006 | Qu et al. |
| 7,108,860 B2 | 9/2006 | Dueva et al. |
| 7,153,996 B2 | 12/2006 | Fagan et al. |
| 7,166,273 B2 | 1/2007 | Chaudhuri |
| 7,175,834 B2 | 2/2007 | Aust et al. |
| 7,179,775 B2 | 2/2007 | Foster |
| 8,632,612 B2 | 1/2014 | Yontz |
| 2003/0007986 A1 | 1/2003 | Stora et al. |
| 2003/0036489 A1 | 2/2003 | Liu et al. |
| 2003/0133895 A1* | 7/2003 | China et al. ............... 424/70.12 |
| 2003/0167681 A1 | 9/2003 | Puche |
| 2004/0018954 A1 | 1/2004 | Su et al. |
| 2004/0052737 A1 | 3/2004 | Hill |
| 2004/0138090 A1 | 7/2004 | Drapier et al. |
| 2004/0147602 A1 | 7/2004 | Smith et al. |
| 2004/0167245 A1 | 8/2004 | Chappelow et al. |
| 2005/0106112 A1 | 5/2005 | Boyd et al. |
| 2005/0245407 A1 | 11/2005 | Ishihara et al. |
| 2006/0134045 A1* | 6/2006 | Cao et al. ................ 424/70.13 |
| 2006/0165622 A1 | 7/2006 | Hiramoto |
| 2006/0207037 A1 | 9/2006 | Fadel et al. |
| 2007/0111917 A1 | 5/2007 | Lang et al. |
| 2007/0161530 A1 | 7/2007 | Kaneda et al. |
| 2007/0298000 A1 | 12/2007 | Grune |
| 2008/0044365 A1 | 2/2008 | Simonnet et al. |
| 2008/0081779 A1 | 4/2008 | Holscher |
| 2008/0124426 A1 | 5/2008 | Kobler et al. |
| 2008/0188603 A1 | 8/2008 | Porzio et al. |
| 2008/0242721 A1* | 10/2008 | Selifonov ...................... 514/467 |
| 2008/0305978 A1 | 12/2008 | Wietfeldt et al. |
| 2009/0035234 A1 | 2/2009 | Cunningham et al. |
| 2009/0053153 A1 | 2/2009 | Lee et al. |
| 2009/0281012 A1 | 11/2009 | Trivedi et al. |
| 2010/0087357 A1 | 4/2010 | Morgan, III et al. |
| 2011/0196081 A1 | 8/2011 | Kwon et al. |
| 2011/0300083 A1 | 12/2011 | Yontz et al. |

FOREIGN PATENT DOCUMENTS

| | | | |
|---|---|---|---|
| DE | 600 03 541 T2 * | 4/2004 | ............... A61K 7/48 |
| EP | 012543 A1 | 6/1980 | |
| EP | 0308956 A2 | 3/1989 | |
| EP | 0507190 A1 | 10/1992 | |
| EP | 0913463 A1 | 5/1999 | |
| JP | 58124711 A | 7/1983 | |
| JP | 59164712 A | 9/1984 | |
| JP | 5320023 A | 12/1993 | |
| JP | 5320042 A | 12/1993 | |
| JP | 07228887 A | 8/1995 | |
| JP | 2005143466 A | 6/2005 | |
| JP | 2006022119 A | 1/2006 | |
| JP | 2006143702 A | 6/2006 | |
| JP | 2009035733 A | 2/2009 | |
| JP | 2009179624 A | 8/2009 | |
| SU | 722912 | 3/1980 | |
| WO | 9412489 A1 | 6/1994 | |
| WO | 9856889 | 12/1998 | |
| WO | 0193813 A2 | 12/2001 | |
| WO | 2005058265 A1 | 6/2005 | |
| WO | 2005095378 A2 | 10/2005 | |
| WO | 2006089873 A1 | 8/2006 | |
| WO | 2007062118 A2 | 5/2007 | |
| WO | 2007062158 A2 | 5/2007 | |
| WO | 2007094922 A2 | 8/2007 | |
| WO | WO2007/145994 * | 12/2007 | ............. C08G 73/00 |
| WO | 2008046795 A1 | 4/2008 | |
| WO | 2008089463 A2 | 7/2008 | |
| WO | WO 2009/006214 * | 1/2009 | ............... A61K 8/02 |
| WO | 2009032905 A1 | 3/2009 | |
| WO | 2009048874 A1 | 4/2009 | |
| WO | 2009065244 A1 | 5/2009 | |
| WO | 2010036884 A1 | 4/2010 | |
| WO | 2010043717 A3 | 4/2010 | |
| WO | 2010096623 A1 | 8/2010 | |
| WO | 2010151558 A1 | 12/2010 | |

OTHER PUBLICATIONS

Extended European Search Report for European Application No. 11781171.1; Search Report Date Dec. 19, 2014; 10 pages.

Bechtold, et al., "Perfectly Alternating Copolymer of Lactic Acid and Ethylene Oxide as a Plasticizing Agent for Polylactide," Macromolecules 34: 8641-8648 (2001).

Black, Cline, et al., "The Solubility of Water in Hydrocarbons", The Journal of Chemical Physics, vol. 16, pp. 537-543 (1948).

(56) References Cited

OTHER PUBLICATIONS

Bozell, et al., "Production of levulinic acid and use as a platform chemical for derived products," Resources, Conservation and Recycling 28: 227-239 (2000).
Brigl, Percy, et al., "The Reaction of the Pyruvic Acid with Glycerin," Annalen der Chemie 476: p. 215-232, Received Oct. 7, 1929, (with English translation).
Chinese Search Report from Second Office Action for Appln. No. 201180023186.7, issued Jun. 20, 2014 (English translation), 12 pages.
Corma, et al., "Chemical Routes for the Transformation of Biomass into Chemicals," Chem. Rev. 107: 2411-2502 (2007).
Cuiling, et al., "Synthesis of Levulinic Ketals with Furfuryl Alcohol as Raw Material," Journal of Huagiao University (Nature Science) 23(3): 257-259 (2002) (English Translation).
Doolittle, Arthur K., "Application of a Mechanistic Theory of Solvent Action to Plasticizers and Platicization", Journal of Polymer Science, vol. 2, No. 2 (1947) 121-141.
Eastman Chemical Company. (May 2006). Selecting Coupling Agents for Multi-phase Models. Retrieved Aug. 13, 2009, from http://www.eastman.com/Literature Center/M/M207.pdf, 16 pages.
Girisuta, Buana, "Levulinic Acid from Lignocellulosic Biomass," Rijksuniversiteit Groningen, pp. 1-148, Nov. 2007.
Gonzalez, et al., "Application of Fourier Transform Infrared Spectroscopy in the Study of Interactions Between PVC and Plasticizers: PVC/Plasticizer Compatibility versus Chemical Structure of Plasticizer," Journal of Applied Polymer Science 101: 1731-17.
Haskelbhrg, L., "The preparation of glycerol esters of amino acids," Compt. rend. 190270-190272 (1930).
Hexyl Cellosolve(R) Solvent, DOW Technical Data Sheet, 3 pages (2012).
Holmberg, Krister, "Surfactants with controlled half-lives", Current Opinion in Colloid & Interface Science, Volumn 1, Issue 5, pp. 572-579 (Oct. 1996).
Horsfall, et al., "Fungitoxicity of Dioxanes, Dioxolanes, and Methylenedioxybenzenes," The Connecticut Agricultrual Experiment Station New Haven, Bulletin 673: pp. 1-44, Jun. 1965.
Hoydonckx, et al., "Esterification and transesterification of renewable chemicals," Topics in Catalysis 27(1-4): 83-96 (2004).
International Search Report for International Application No. PCT/US2011/035956, Application Filing Date May 10, 2011, Date of Mailing Feb. 8, 2012, 4 pages.
International Search Report for International Application No. PCT/US2011/035973, Application Filing Date May 10, 2011, Date of Mailing Feb. 8, 2012, 6 pages.
Krauskopf, Leonard G., "How About Alternatives to Phthalate Plasticizers?," Journal of Vinyl & Additive Technology 9 (4): 159-171 (2003).
Ma, et al., "Biodiesel production: a review," Bioresource Technology 70: 1-15 (1999).
Meher, et al., "Technical aspects of biodiesel production by transesterification—a review," RSER 194: 1-21 (2004).
Meltzer, et al., "2,2-Disubstituted 1,3-Dioxolanes and 2,2-Disubstituted 1,3-Dioxanes," JOC 25: 712-715 (1960).
Meskens, Frans A.J., "Methods for the Preparation of Acetals from Alcohols or Oxiranes and Carbonyl Compounds," Synthesis 501-522 (1981).
Miller, et al., "Biorenewable Fuels and Chemicals via Reactive Distillation," Midtech Midland, May 11, 2006 ( Powerpoint Presentation) 17 pages.
Moncrieff, R.W., "Ketals," The Journal of the American Oil Chemist's Society 259-261 (1947).
Olson, Edwin S., "Subtask 4.1—Conversion of Lignocellulosic Material to Chemicals and Fuels," Final Report for U.S. Dept. of Energy, National Energy Technology Laboratory, Cooperative Agreement No. DE-FC26-98FT40320 (Jun. 2001) 16 pages.
Ono, et al., "Synthesis and Properties of Soap Types of Cleavable Surfactants Bearing a 1,3-Dioxolane Ring Derived from Long-chain Epoxides and Ethyl Levulinate," J. Jpn. Oil Chem. Soc. 42(12): 965-971 (1993).
Showier, et al., "Condensation Products of Glycerol with Aldehydes and Ketones. 2-Substituted m-Dioxan-5-OLS and 1,3-dioxolane-4-methanols," Chem. Rev. 67: 427-440 (1967).
STIC Search Report dated Jul. 5, 2013, 90 pages.
Takenishi, et al., The Syntheses from Levulinic Acid. A Possible Use of Some 2 Methyl-5-oxopyrrolidine-2 carboxylic Esters as Plasticizers, 27(4): 207-209 (1954).
The Good Scents Company, "ethyl leuvlinate propylene glycol ketal", from http://www.thegoodscentscompany.com/data/rw1597311.html, 2 pages (2011).
Timokhin, et al., "Levulinic acid in organic synthesis," Russian Chemical Reviews 68(1) 73-84 (1999).
Wardzinska, et al., "Influence of the Glycol Component in Dibenzoate Plasticizers on the Properties of Plasticized PVC Films," Journal of Applied Polymer Science 97: 822-824 (2005).
Werpy, et al., "Top Value Added Chemicals from Biomass—vol. I—Results of Screening for Potential Candidates from Sugars and Synthesis Gas," Biomass 1-69 (2004).
Wood, et al., "Cyclic polyesters: 1. Preparation by a new synthetic method, using polymer-supported reagents," Polymer 34(14): 3052-3058 (1993).
Written Opinion for International Application No. PCT/US2011/035956, Application Filing Date May 10, 2011, Date of Mailing Feb. 8, 2012, 6 pages.
Written Opinion for International Application No. PCT/US2011/035973, Application Filing Date May 10, 2011, Date of Mailing Feb. 8, 2012, 7 pages.
Yamaguchi, Masahiko, "Synthesis of Polycyclic Aromatic Compounds via Polyketides," Yuki Gosei Kagaku Kyokaishi 45(10) 969-982 (1987) (Chinese—Translation of Abstract Only).
Yang, et al., "Investigation of homopolymerization rate of perfluoro-4,5-substituted-2-methylene-1,3-dioxolane derivatives and properties of the polymers," Journal of Flourine Science 127: 277-281 (2006).
Zhang, et al., "Synthesis of Ketals of 4-Oxopentanoates," Lanzhou Daxue Xuebao, Ziran Kexueban 30(2): 66-70 (1994).
Japan Notice of Reasons for Rejection for Japan Application No. 2013-510256; Rejection Date Mar. 13, 2015; Mailing Date: Mar. 24, 2015, 6 pages, English Translation begins on p. 4.
Girisuta, et al., "Green Chemicals A Kinetic Study on the Conversion of Glucose to Levulinic Acid," Chemical Engineering Research and Design 84(A5) 339-349 (2006).
Girisuta, et al., "Kinetic Study on the Acid-Catalyzed Hydrolysis of Cellulose to Levulinic Acid," Ind. Eng. Chem. Res. 46: 1696-1708 (2007).

* cited by examiner

PERSONAL CARE FORMULATIONS CONTAINING ALKYL KETAL ESTERS AND METHODS OF MANUFACTURE

CROSS-REFERENCE TO RELATED APPLICATIONS

This application is a divisional of U.S. Ser. No. 13/104,570, filed May 10, 2011, which claims the benefit of U.S. Provisional Application No. 61/332,978, filed May 10, 2010, and to U.S. Provisional Application No. 61/332,982, filed May 10, 2010, all of the foregoing being incorporated herein by reference in their entirety.

FIELD OF THE INVENTION

This invention relates to personal care formulations that contain certain alkyl ketal ester compounds and to methods for the manufacture of the formulations.

BACKGROUND

Personal care formulations are available in a wide range of formulation forms and are used in a wide variety of specialized applications. Because these various types of formulations differ enormously, as do the conditions under which they are used, the individual formulations tend to be formulated specifically for the end-use application for which they are intended. Further, the use of materials based on renewable resources is becoming of increasing interest as formulators redesign their formulations to meet environmental sensitivities of their consumer bases.

SUMMARY

Disclosed herein are personal care formulations, the personal care formulations comprising an alkyl ketal ester having the structure

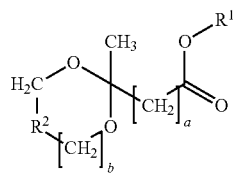

wherein a is 0 or an integer of 1 to 12, b is 0 or 1, $R^2$ a divalent $C_{1-8}$ group optionally substituted with up to 5 hydroxyl groups, and $R^1$ is $C_{1-6}$ alkyl; and an active agent selected from organic anti-aging agents, organic anti-acne agents, organic skin whiteners, organic ultraviolet light absorbers, organic tanning agents, organic anti-alopecia agents, antifungal agents, anti-dandruff active agents, antimicrobial agents, organic medicinals, depilatory compounds, hair dyes, organic insect repellants, and combinations thereof.

Also disclosed is a waxy personal care formulation comprising a wax, an emollient, and an alkyl ketal ester of structure I.

In another embodiment, a personal care formulation in the form of an emulsion comprises (i) a continuous phase and a disperse phase wherein the continuous phase or the disperse phase is an aqueous phase and the other is an oil phase; or at least two co-continuous phases wherein at least one of the co-continuous phases is an aqueous phase and at least one of the co-continuous phases is an oil phase; and wherein any of the foregoing oil phases comprises at least one of (a) a paraffinic, naphthenic or aromatic mineral oil, (b) a nonionic organic compound having a melting temperature of less than 45° C., a molecular weight of at least 190 Daltons, an amido or ester group, and an alkyl chain containing at least 8 carbon atoms, and a solubility in water of no greater than 1 part in 99 parts of water, (c) a nonionic organosilicone compound having a melting temperature of less than 45° C., and a solubility in water of no greater than 1 part in 99 parts of water, (d) a long chain alcohol, or (e) a wax; and (ii) an alkyl ketal ester of structure I.

In still another embodiment, a personal care formulation comprises an alkyl ketal ester of structure I, and an additional cosmetically acceptable ingredient.

The invention is further illustrated by the following Detailed Description, Examples, and Claims.

DETAILED DESCRIPTION

We have found that certain alkyl ketal esters of Structure I are excellent formulatory ingredients that provide benefit in a wide number of personal care formulations. The alkyl ketal esters are excellent solvents for a wide range of materials, including active agents useful in personal care formulations. Many of them are at least partially miscible with water or other organic solvents, or both, as well as a wide range of somewhat hydrophobic materials as are commonly present in personal care formulations. The alkyl ketal esters have low volatility. Under normal conditions of manufacture, storage, and use, the alkyl ketal esters are not reactive with many of the other materials that are commonly found in personal care formulations.

Because of these attributes, the alkyl ketal esters are useful in a wide range of personal care formulations, including formulations that contain various types of active agents as described below, as well as formulations that do not contain such active agents. The alkyl ketal esters can provide a range of benefits to the formulation. The particular benefits seen in any given formulation will depend on the particular ingredients and function of that formulation.

In an embodiment, the alkyl ketal esters of structure I can be used to enhance the solubility of an active agent in a personal care formulation. Depending on the native solubility of the active agent in the formulation and the type of formulation, the alkyl ketal ester can be used as a cosolvent with water, as a compatibilizer with water and an organic solvent, as a cosolvent with an organic solvent, as an emulsifier, or a combination comprising of any of one or more of the foregoing. As is known to those of skill in the art of formulating personal care products, an individual ingredient can have more than one type of function, for example a given alkyl ketal ester could function both as a cosolvent and as a compatibilizer.

When the active agent has limited water solubility, the alkyl ketal ester can in some embodiments function as a cosolvent, together with water. Many alkyl ketal esters are good solvents for active agents and also have good miscibility in water. The presence of such an alkyl ketal ester can allow the concentration of the active agent to be increased, often without the presence of volatile organic compounds (VOCs) such as ethanol, isopropanol, acetone, ethyl acetate, and the like in the formulation. The result in some cases can be a more concentrated low VOC formulation. The alkyl ketal ester can also perform additional functions, such as compatibilization of aqueous and organic phases, compatibilization or solubilization of certain organic materials into an aqueous phase, emulsification of an oil phase into an aqueous phase or of an aqueous phase into an oil phase.

The alkyl ketal ester can act as an emulsifier, compatibilizer, or solubilizer for ingredients other than the active agent, or as a co-emulsifier, co-compatibilizer, or co-solubilizer for ingredients other than the active agent, in particular if the alkyl ketal ester is highly water-soluble. Moreover, incorporation of the alky ketal ester can lead to a lighter, less greasy or heavy-feeling formulation, especially compared to many other naturally-derived ingredients.

In cases in which the active agent is somewhat soluble or highly soluble in an alcohol or alcohol-water mixture, the alkyl ketal ester can in some cases function as a cosolvent, either with the alcohol or with an alcohol-water mixture. The alkyl ketal ester can in some cases permit an increase in the concentration of the active agent in an alcoholic or alcohol-water phase. In other cases, it can permit the proportion of the alcohol in the cosolvent mixture to be decreased, which has the benefit of reducing VOCs in the formulation and in some cases decreasing the drying effect the formulation has on the skin. As with the aqueous systems, the alkyl ketal ester can perform additional functions, such as compatibilization, solubilization, or emulsification. In some cases, the alkyl ketal ester can also lead to a lighter, less greasy or heavy-feeling formulation, as before.

In formulations containing active agents that are oil or oil-soluble and sparingly (if at all) soluble in water, the alkyl ketal ester can in some cases permit the active agent to become dissolved in an aqueous phase, in some cases alone and in other cases in conjunction with one or more other cosolvents. This can in some cases allow a highly water-insoluble active agent to become incorporated into an aqueous-based solution or gel-type form. In some cases, mixtures of alkyl ketal esters having different solubility/solubilizing characteristics can be present in order to accomplish the dissolution of the active agent. Alternatively (or in addition), the alkyl ketal ester can aid in dissolving or compatibilizing such an active agent into an organic phase, or to help compatibilize or emulsify an organic phase containing the active agent with an aqueous phase, forming in this case an emulsified formulation that can be, for example, a cream or lotion. As before, the alkyl ketal ester in some cases can allow the level of emollient materials to be reduced or improve formulation feel characteristics.

Whether an active agent is present or not, the alkyl ketal ester can in some cases aid mutually incompatible materials to be formulated into a stable formulation form. Thus, the alkyl ketal ester is a valuable ingredient in many emulsified formulations, such as lotions and creams, which include a water-in-oil or oil-in-water emulsion. Also, the alkyl ketal ester in many cases can allow hydrophobic organic ingredients to be dissolved into an aqueous phase to produce clear formulations. In many cases, this can be achieved while reducing or eliminating other ingredients from the formulation. For example, volatile organic compounds or emulsifiers can be eliminated or used in reduced quantities. The presence of the alkyl ketal ester can improve the feel of a cosmetic, giving the formulated formulation a lighter, less oily feel while preserving its function and performance. In many cases, formulation viscosity is reduced, which can contribute to the lighter and less greasy feel.

Because the alkyl ketal ester is a good solvent for a wide range of materials, it is very useful for making concentrates, which can be let down into water, an alcohol or other diluent.

Still another benefit of the alkyl ketal ester in some formulations is that it allows the amount of water to be increased in otherwise highly hydrophobic formulations. This can provide a moisturizing function in some cases, or provide other benefits. A notable example of this is in lip care formulations, particularly lipsticks, lip glosses, and lip balms, and cuticle balms which are based on waxes and other highly hydrophobic materials. The alkyl ketal ester permits up to 3%, up to 4%, up to 5%, or up to 10% by weight of water to be included in the lip care or cuticle care formulation, which can allow the lip care or cuticle care formulation to perform a hydrating function.

In one aspect, this invention is a formulated personal care formulation comprising an alkyl ketal ester of structure I, and one or more active agent selected from organic anti-aging agents, organic anti-acne agents, organic skin whitening agents, organic ultraviolet light absorbing agents, organic tanning agents, organic anti-alopecia agents, anti-fungal agents and/or anti-dandruff agents, antimicrobial agents, organic medicinals, depilatory compounds, hair dyes, or organic insect repellants. In certain embodiments, the alkyl ketal ester forms part of a cosolvent mixture with water or with another organic solvent miscible with the alkyl ketal ester at the relative proportions thereof that are present in the formulated personal care formulation, and the active agent is dissolved in the cosolvent mixture. The active agents are present in amounts effective to achieve the desired activity, which can vary broadly, depending on the active agent and the product. Thus, an active agent can be present in the formulation in amounts as low as 0.001% by weight, 0.01% by weight, or 0.1% by weight, up to 30% by weight. The amount of water used in the formulation can also vary widely based on the active agent and the product, from anhydrous products as described above, to products have from 2 to 90%, 80%, 70%, 60%, 50%, 40%, 30%, 20%, or 10% by weight of water, based on the total weight of the formulation.

Thus, in some embodiments, the formulated personal care formulation includes a compound selected from alpha-hydroxy acids such as lactic acid, 2-hydroxydecanoic acid, 2-hydroxyoctanoic acid and glycolic acid, beta-hydroxy acids such as beta-hydroxy salicylic acid, avobenzone, coenzyme Q10, benzoate-4-methylbenzylidene, cinoxate, dioxybenzone, homosalate, menthyl anthranilate, mexoryl SX, drometrizole trisiloxane, octocrylene, octyl methoxycinnamate, ethylhexyl salicylate, oxybenzone, padimate O, p-aminobenzoic acid (PABA), phenylbenzimidazole sulfonic acid, sulisobenzone, titanium trolamine salicylate, salicylic acid, retinoic acid (including the all-trans isomer known as tretinoin), benzoyl peroxide, hydroquinon, arbutun (including plant extracts containing same), kojic acid, azelaic acid, glycyrrhetic acid, levulinic acid, 2-cyano-3,3-diphenylacrylic acid, sodium benzotriazolyl butylphenol sulfonate, ethyl-2-cyan-3,3-diphenylacrylate, 2-t-butyl-6-(5-chloro-2H-benzotriazol-2-yl)-p-cresol, 2-(2-H-benzotriazol-2-yl)-4-methylphenol, benzophenone-12, bornelone, or 2-benzotriazolyl-4-tert-octylphenol. These compounds function as anti-aging, anti-acne, skin whitening and/or UV absorbers; formulations containing them are useful as anti-aging or anti-wrinkle formulations, acne treatments, skin whiteners, and/or sunscreens.

In certain embodiments, a personal care formulation includes a tanning agent such as dihydroxyacetone, erythrulose, dihydroxyacetone-ortho-ethyl-acetate, canthaxanthin, or afamelanotide. These compounds function as tanning agents, and personal care formulations containing them in sufficient quantities are effective tanning (skin darkening) formulations.

In some embodiments, the personal care formulation includes a compound selected from minoxidil and 5-alpha reductase inhibitors such as dutasteride and ketoconazole. These compounds function as anti-alopecia (hair loss prevention) agents; accordingly, personal care formulations containing them are useful in some cases to prevent hair loss.

In certain embodiments, a personal care formulation includes a compound selected from zinc pyrithione, selenium sulfide, clotrimazole, tea tree oil, or piroctone olamine. These compounds function as anti-fungal agents, and personal care formulations containing them in sufficient quantities are effective topical anti-fungal treatments (such as for *Tinea pedis* or *Tinea cruris*) and/or as anti-dandruff formulations.

In certain embodiments, a personal care formulation includes a compound selected from an amphetamine, an antihistamine, methylphenidate, oxymetazoline, tetrahydrolzoline hydrochloride, or psilocybin. These compounds function as vasoconstrictors in some instances and personal care formulations containing them in sufficient quantities are effective as redness reducers (such as in eye drops and anti-redness or anti-puffing creams).

In certain embodiments, a personal care formulation includes a compound selected from calcium thioglycolate, sodium thioglycolate, thioglycolic acid, ammonium thioglycolate, butyl thioglycolate, ethanolamine thioglycolate, glyceryl thioglycolate, isooctyl thioglycolate, isopropyl thioglycolate, magnesium thioglycolate, methyl thioglycolate, or potassium thioglycolate. These compounds function to modify hair fibers by breaking S—S bonds in keratin; personal care formulations containing them in sufficient quantities are used in depilatories, permanent waves, relaxers, hair straightening, and hair re-styling formulations.

In certain embodiments, a personal care formulation includes a compound selected from aluminum zirconium tetrachlorohydrex gly, aluminum chlorohydrate, or aluminum chloride. These agents are anti-perspirants and personal care formulations containing these are often effective as deodorants and anti-perspirants.

In certain embodiments, a personal care formulation includes a compound selected from resorcinol ("resorcin"), 1-napthol, p-aminophenol, p-phenylenediamine (and its salts), 4-amino-2-hydroxytoluene, and the like. These active agents are effective hair dyes; and personal care formulations containing these are often effective as hair colorants or hair colorant concentrates.

In certain embodiments, a personal care formulation includes a compound selected from phenoxyethanol, N,N-diethyl-m-toluamide, p-menthane-3,8-diol (active agent in the essential oil of lemon eucalyptus), nepetalactone (catnip oil), citronella oil, permethrin, neem oil, or bog myrtle extract. These active agents are effective insect repellants; and personal care formulations containing these are often effective as insect repellants.

In some embodiments, the personal care formulation comprises from 0 or 0.001 to 15% by weight of water, specifically, 0 or 0.01 to 12 wt % by weight of water, 0.1 to 10% by weight water, 0.5 to 8% by weight water, or 1 to 5% by weight of water, each based on the total weight of the formulation. In some embodiments, the personal care formulation is essentially anhydrous, containing no more than 3% by weight water, no more than 2% by weight water, more specifically no more than 1% by weight water. In essentially anhydrous personal care formulations, the amount of water can be 0%, as low as 0.001%, or 0.01%, or 0.1% by weight, each based on the total weight of the personal care formulation.

In another aspect, for use in a waxy formulation, e.g., a lipstick, lip gloss, lip balm formulation, or a cuticle cream, that contains a wax, an emollient, and an alkyl ketal ester of structure I is provided. In embodiments of particular interest, the lipstick, lip gloss, lip balm, or cuticle cream formulation contains from 0.1 to 10% by weight water, specifically 0.5 to 5% by weight water, each based on the total weight of the persona care formulation. These formulations are in stick or other solid form. The alkyl ketal ester preferably is a partially or fully water-miscible alkyl ketal ester, as defined below, when the waxy formulation contains more than 0.1% by weight water.

In another aspect, a formulated personal care formulation in the form of an emulsion is provided. The emulsion can have a continuous phase and a disperse phase, one of which is an aqueous phase, and the other of which is an oil phase. Alternatively, the emulsion can have at least two co-continuous phases, again wherein at least one of the co-continuous phase is an aqueous phase and at least one of the co-continuous phases is an oil phase. The oil phase contains at least one of (a) a paraffinic, naphthenic or aromatic mineral oil, (b) a nonionic organic compound having a melting temperature of less than 45° C., a molecular weight of at least 190 Daltons, an amido or ester group, an alkyl chain containing at least 8 carbon atoms, and a solubility in water of no greater than 1 part in 99 parts of water by weight; (c) a nonionic organosilicone compound having a melting temperature of less than 45° C. and a solubility in water of no greater than 1 part in 99 parts of water by weight; (d) a long chain alcohol; and (e) a wax. The emulsion further comprises an alkyl ketal ester of structure I. The alkyl ketal ester can be present in a continuous phase, a disperse phase, in both a continuous phase and a disperse phase, or at the interface between a continuous and a disperse phase.

Personal care formulations and products can take the physical form of solids (sticks, bars, powders, etc.), solutions (including solutions containing sufficient gallant or thickener to provide a gel-like consistency), ointments, dispersions (including pastes), or emulsions (including gels, liniments, lotions, creams, or the like). They can be sprayable, in particular the solutions, dispersions, and powders. The personal care products can be, for example, bath or shower products, including various hair and body cleaners; eye care products; cosmetics; a fragrance; treatment formulation, including a hair coloring formulation and a; a hair straightening or permanent wave formulation; a nail care formulation; an oral hygiene formulation, including toothpaste and mouthwash; a shave cream; a skin care formulation; a sun care formulation; a lip care formulation; an antiperspirant; or a foot care formulation.

The alkyl ketal esters useful herein include those having the general structure I

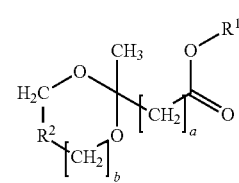

I wherein a is 0 or an integer of 1 to 12, specifically 1 to 6, more specifically 1 to 4;

b is 0 or 1;

$R^2$ is a divalent $C_{1-8}$ group optionally substituted with up to 5 hydroxyl groups, specifically methylene, ethylidene (>CH—CH$_3$), >CH—CH$_2$OH, >C(CH$_3$)CH$_2$OH, >C(C$_2$H$_5$)CH$_2$OH, >C(CH$_2$OH)$_2$, >CH—CH(OH)—CH$_2$OH, or >CH—(CHOH)$_3$—CH$_2$OH; and $R^1$ is $C_{1-6}$ alky, specifically a $C_{1-4}$ alkyl, more specifically a $C_{1-2}$ alkyl.

Some compounds within the scope of Structure I contain one or more chiral carbon atoms, as is the case where b is 0 or $R^2$ is substituted; structure I does not distinguish among those possible stereoisomers and is intended to include all such stereoisomers. In a specific embodiment, a is 1 to 4, B is 0 or 1, and $R^2$ is >CH—CH$_3$, >CH—CH$_2$OH, >C(CH$_3$)CH$_2$OH, >C(C$_2$H$_5$)CH$_2$OH, >C(CH$_2$OH)$_2$, >CH—CH(OH)—CH$_2$OH, or >CH—(CHOH)$_3$—CH$_2$OH.

When b is 0, the alkyl ketal ester includes a five-membered ring; when b is 1, it includes a six-member ring. In a specific embodiment b is 0.

In some embodiments, b is 0 and $R^2$ is one of methylene, ethylidene or >CH—CH$_2$OH. In other embodiments, b is 1 and $R^2$ is methylene.

In an embodiment, $R^1$ contains 1 or 2 carbon atoms.

Specific alkyl ketal esters include those corresponding to the reaction formulations of 1,2-ethylene glycol with the methyl, ethyl, n-propyl or n-butyl ester of levulinic acid; of 1,2-propylene glycol with the methyl, ethyl, n-propyl or n-butyl ester of levulinic acid; of 1,3-propane diol with the methyl, ethyl, n-propyl or n-butyl ester of levulinic acid; of glycerine with the methyl, ethyl, n-propyl, or n-butyl ester of levulinic acid; of trimethylolethane with the methyl, ethyl, n-propyl, or n-butyl ester of levulinic acid; of trimethylolpropane with the methyl, ethyl, n-propyl, or n-butyl ester of levulinic acid; of pentaerythritol with the methyl, ethyl, n-propyl, or n-butyl ester of levulinic acid; of erythritol with the methyl, ethyl, n-propyl, or n-butyl ester of levulinic acid; of sorbitol with the methyl, ethyl, n-propyl, or n-butyl ester of levulinic acid; of 1,2-ethylene glycol with methyl, ethyl, n-propyl, or n-butyl acetoacetate; of 1,2-propylene glycol with methyl, ethyl, n-propyl, or n-butyl acetoacetate; of 1,3-propane diol with methyl, ethyl, n-propyl, or n-butyl acetoacetate, of glycerine with methyl, ethyl, n-propyl, or n-butyl acetoacetate; of trimethylolethane with methyl, ethyl, n-propyl or n-butyl acetoacetate; of trimethylolpropane with methyl, ethyl, n-propyl, or n-butyl acetoacetate, or erythritol with methyl, ethyl, n-propyl, or n-butyl acetoacetate; of pentaerythritol with methyl, ethyl, n-propyl, or n-butyl acetoacetate; or of sorbitol with methyl, ethyl, n-propyl, or n-butyl acetoacetate.

Specific alkyl ketal esters include those having the following structures II-VI. An embodiment includes alkyl ketal esters of structure II

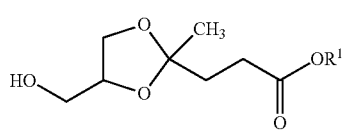

(II)

wherein $R^1$ is methyl, ethyl, n-propyl, or n-butyl. When $R^1$ is methyl, this structure is referred to herein as "methyl-LGK," and corresponds to the reaction formulation of methyl levulinate with glycerine. Methyl-LGK is miscible with water in all proportions.

When $R^1$ in structure II is ethyl, this structure is referred to herein as "ethyl-LGK," or "Et-LGK" and corresponds to the reaction formulation of ethyl levulinate with glycerine. Ethyl-LGK is miscible in water in all proportions. Ethyl-LGK also dissolves or is miscible with a large number of hydrophobic and hydrophilic organic compounds to the extent of at least 20 parts of the organic compound in 80 parts of ethyl-LGK. Examples of such organic compounds include methanol, ethanol, tetrahydrofuran, acetone, ethyl acetate, ethyl laurate, lauric acid, methylene chloride, toluene, acetic acid, low molecular weight poly(propylene glycol), and castor oil.

When $R^1$ in structure II is n-propyl, this structure is referred to herein as "n-propyl-LGK," and corresponds to the reaction formulation of n-propyl levulinate with glycerine. n-Propyl-LGK is miscible with water to the extent of 1 part per 99 parts water.

When $R^1$ in structure II is n-butyl, this structure is referred to herein as "n-butyl-LGK" or "Bu-LGK," and represents the reaction formulation of n-butyl levulinate with glycerine. n-Butyl-LGK is miscible in water to the extent of 1 part per 99 parts of water. It dissolves or is miscible with various organic compounds to the extent of at least 20 parts of the organic compound in 80 parts of N-butyl-LGK. Examples of such organic compounds include alcohols (including ethanol and 1,2-butylene glycol), organic esters (such as $C_{12-14}$ alkyl benzoates, isopropyl myristate and octyl palmitate), and many vegetable oils (including castor, corn, soy and safflower oils).

Another embodiment includes alkyl ketal esters of structure III

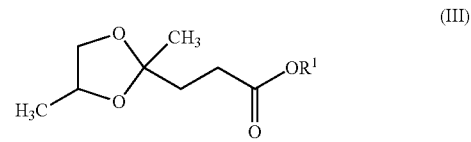

(III)

wherein $R^1$ is methyl, ethyl, n-propyl, or n-butyl. When $R^1$ is methyl, the structure is referred to herein as "methyl-LPK" and corresponds to the reaction formulation of methyl levulinate with 1,2-propylene glycol.

When $R^1$ in structure III is ethyl, this structure is referred to herein as "ethyl-LPK" or "Et-LPK," and corresponds to the reaction formulation of ethyl levulinate with 1,2-propylene glycol. Ethyl-LPK is miscible in water to the extent of 2.5 parts in 97.5 parts of water. Ethyl-LPK dissolves or is miscible with a variety of organic compounds of varying hydrophilicity, to the extent of at least 20 parts of the organic compound in 80 parts of ethyl-LPK. These organic compounds include, for example, methanol, ethanol, tetrahydrofuran, acetone, ethyl acetate, methylene chloride, toluene, cyclohexane, acetic acid, low molecular weight poly(propylene glycol), mineral oil, castor oil, canola oil, corn oil, and sunflower oil.

When $R^1$ in structure III is n-butyl, this structure is referred to herein as "n-butyl-LPK" or "Bu-LPK," and represents the reaction formulation of n-butyl levulinate with 1,2-propylene glycol. n-butyl-LPK dissolves or is miscible with various organic compounds to the extent of at least 20 parts of the organic compound in 80 parts of N-butyl-LPK by weight. Examples of such organic compounds include alcohols (including ethanol and 1,2-butylene glycol), organic esters (such as $C_{12-14}$ alkyl benzoates, isopropyl myristate and octyl palmitate), and many vegetable oils (including castor, corn, soy and safflower oils). n-butyl-LPK dissolves or is miscible with water to the extent of about 99 parts of water to about 1 part of the part of the N-butyl-LPK by weight.

Another embodiment includes alkyl ketal esters of structure IV

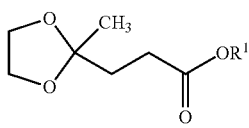

(IV)

wherein $R^5$ is methyl, ethyl, n-propyl, or n-butyl. When $R^1$ is ethyl, this structure is referred to herein as "ethyl-LEK," and corresponds to the reaction formulation of ethyl levulinate with 1,2-ethylene glycol. Ethyl-LEK is miscible in water to the extent of 5 parts per 95 parts of water by weight.

Another embodiment includes alkyl ketal esters of structure V

(V)

wherein $R^5$ is methyl, ethyl, n-propyl, or n-butyl. When $R^1$ is methyl, this structure is referred to herein as "Me-AcAcGK," and represents the reaction formulation of methyl acetoacetate with glycerine. When $R^1$ is ethyl, this structure is referred to herein as "Et-AcAcGK," and represents the reaction formulation of ethyl acetoacetate with glycerine. Me-AcAcGK and Et-AcAcGK each are miscible with water in all proportions.

Another embodiment includes alkyl ketal esters of structure VI

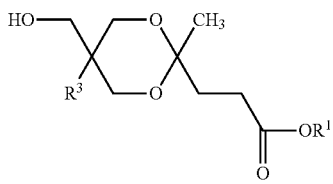

(VI)

wherein $R^1$ is methyl, ethyl, n-propyl or n-butyl and $R^3$ is methyl or ethyl. Compounds according to structure VI correspond to the reaction formulation of trimethylolethane ($R^3$ is methyl) or trimethylolpropane ($R^3$ is ethyl) and a $C_{1-6}$ ester of levulinic acid. When $R^1$ is ethyl, and $R^3$ is methyl, this structure is referred to herein as "ethyl-LTMEK," and when $R^1$ is ethyl, and $R^3$ is ethyl, this structure is referred to herein as "ethyl-LTMPK."

The alkyl ketal esters of structures I-VI can be prepared by reacting an alkyl keto ester of structure VII

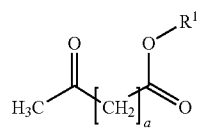

(VII)

with the appropriate polyol of structure VIII

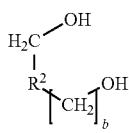

I wherein a, b, $R^2$ and $R^1$ are as defined in structure I. Specific ketoesters include $C_1$-$C_4$ alkyl esters of pyruvic acid, acetoacetic acid, levulinic acid, α-ketobutyric acid, α-ketoisovaleric acid, 5-ketohexanoic acid, α-ketoisocaproic acid, 4-acetylbutyric acid, 2-ketopentanoic acid, 3-ketohexanoic acid, 4-ketohexanoic acid, 2-ketooctanoic acid, 3-ketooctanoic acid, 4-ketooctanoic acid, 7-ketooctanoic acid, 2-keto-4-pentenoic acid, and 2-oxo-3-butynoate. Specific polyols include ethylene glycol, 1,2-propylene glycol, 1,3-propane diol, glycerine, trimethylolethane, trimethylolpropane, erythritol, pentaerythritol, or sorbitol, although reaction conditions must be controlled to produce the monoderivatives of the last three compounds. This reaction can be performed in the presence of an acid catalyst. A preferred process is described in WO 09/032,905.

In preferred embodiments, the keto ester is a $C_1$-$C_4$ alkyl ester of levulinic acid (4-oxopentanoic acid). Levulinic acid is an abundant feedstock that is prepared on an industrial scale by acidic degradation of hexoses and hexose-containing polysaccharides such as cellulose, starch, sucrose, and the like. Other preferred keto esters include $C_1$-$C_4$ alkyl esters of pyruvic acid and acetoacetic acid. Especially preferred keto esters include ethyl levulinate, n-propyl levulinate, and n-butyl levulinate.

The term "miscible" and its variations ("miscibility", "compatibility", and the like) are used herein as a synonym for "soluble", i.e., a mixture of the materials by themselves form a "true" solution, in which one material is molecularly dispersed in the other, or in which one material is dispersed as droplets which have a longest dimension of less than 200 nm, such that the mixture is optically clear. In an exemplary embodiment, the longest dimension is a "radius of gyration." As used herein, a material that is "miscible" or "fully miscible" in another, without further qualification, is miscible with that other material in all proportions, i.e., in mixtures that contain the two components by themselves in all weight ratios from 99:1 to 1:99. A fully miscible alkyl ketal ester is soluble in another material, such as water, at all proportions from 99:1 to 1:99. A partially miscible alkyl ketal ester is immiscible in another material in proportions from greater than 30 parts of the alkyl ketal ester in 70 parts or less of the other material and miscible in other combinations. A sparingly miscible alkyl ketal ester is immiscible in another material or miscible in another material to the extent of less than 10 parts in 90 parts of the other material. A material is "immiscible" in another if it is not soluble by itself in that material to the extent of at least 1 part per 99 parts of the other. Unless stated otherwise, miscibility is assessed at 25° C. The foregoing alkyl ketal esters can be classified as fully water-miscible, partially water-miscible, or sparingly water-miscible. By "macroscopically uniform," it is meant that the formulation is uniform when viewed at a length scale of at least 10 micrometers.

The selection of a particular alkyl ketal ester for a particular personal care formulations will depend at least in part upon the function that the alkyl ketal ester is expected to perform in the formulation, as well as the other ingredients of the formulation. For example, when the alkyl ketal ester is present to solubilize an active agent into an aqueous phase, a partially- or fully-water miscible alkyl ketal ester is selected. If the active agent is highly hydrophobic, a mixture of a partially- or fully-water miscible alkyl ketal ester with a sparingly water-miscible alkyl ketal ester can be used.

When the alkyl ketal ester is present to solubilize an active agent into an alcoholic phase or an alcohol/water mixture, the alkyl ketal ester is preferably miscible in the alcohol to the extent of at least 10 parts of the alkyl ketal in 90 parts of alcohol by weight, specifically 30 parts of the alkyl ester in 70 parts by weight of the alcohol, and can be fully miscible in the alcohol. Alkyl ketal esters that are fully or partially soluble in the alcohol can be present in a mixture with one or more alkyl ketal esters that are only sparingly soluble in the alcohol. This can allow, for example, the alcohol/miscible alkyl ketal ester mixture to function as a cosolvent mixture in which the sparingly soluble alkyl ketal ester is dissolved, such as the case of Et-LPK in a mixture of Et-LGK/1,3-propanediol/water. That other material can be organic compound that is not very soluble in the alcohol, such as a fat or oil, or as shown in one of the examples, a polymer such as polymethylmethacrylate. In some alcoholic systems and alcohol/water systems, the alkyl ketal ester performs a compatibilization and/or emulsification function, such as to compatibilize or emulsify aqueous and oil phases in an emulsion. The alcohol in such an alcoholic phase or alcohol/water mixture is a lower alcohol as described under section (m) below, and is preferably ethanol, 1,2-propylene glycol, glycerol, or 1,3-propane diol.

When the alkyl ketal ester is present to dissolve an active agent into an oil phase, the alkyl ketal ester can be a water-immiscible ketal, a partially-water miscible type or a sparingly water-miscible type. It is also possible in some cases to use fully-water-miscible types in that instance.

When the formulation form is an aqueous solution (containing, for example, at least 35% by weight water based on the weight of the personal care formulation) or an aqueous gel formulation in which an active agent is dissolved, the alkyl ketal ester is preferably a fully water-miscible type such as methyl-LGK, ethyl-LGK, methyl-AcAcGK, or a mixture of one or more of them with a partially water-miscible alkyl ketal ester and/or a sparingly soluble alkyl ketal ester such as propyl-LGK, ethyl-LPK, ethyl-LEK and the like. A partially water-miscible alkyl ketal ester and/or a sparingly soluble alkyl ketal ester such as propyl-LGK, ethyl-LPK, ethyl-LEK and the like can also be used in aqueous solutions at concentrations beyond their miscibility limits if another water miscible co-solvent is present, for example ethanol, isopropanol, or the like.

Formulations that take the form of alcohol or alcohol-water solutions in which an active agent is dissolved, can contain, such as in the case of ethanol and 1,2-propylene glycol, fully water-miscible alkyl ketal esters, partially water-miscible alkyl ketal esters, sparingly water-miscible alkyl ketal esters, or mixtures thereof. When the alcohol is 1,3-propane diol, at least partially water-miscible alkyl ketal esters are preferred, as these tend to be more soluble in 1,3-propane diol. Partially and fully water-miscible alkyl ketal esters can form a single-phase solution with ethanol, 1,2-propylene glycol, and/or 1,3-propane diol, into which additional active agents can be dissolved, or an organic phase can be dispersed. A sparingly water miscible ketal can be used with 1,3-propane diol and water when combined with coupling agents, like ethanol or a fully-water miscible alkyl ketal ester. Gels containing alcohol or alcohol-water solutions in which a gel is suspended can similarly contain fully water-miscible alkyl ketal esters, partially water-miscible alkyl ketal esters, sparingly water-miscible alkyl ketal esters, or mixtures thereof, depending on the alcohol used as described above for alcohol and alcohol-water solutions. The alcohol water-solutions can contain from 1 to 99%, 20 to 80%, 30 to 70%, or 40 to 60% by weight of the alcohol and correspondingly from 99 to 1%, 80 to 20%, 70 to 30%, or 60 to 40% by weight of the water, based on the weight of the alcohol and the water.

Formulations in the form of an emulsion of an oil phase and an aqueous phase (including, for example, lotions and creams) and in which the alkyl ketal ester performs a compatibilizing or emulsifying function between the phases can contain a fully water-miscible alkyl ketal ester such as methyl-LGK, ethyl-LGK, methyl-AcAcGK, or partially water-miscible type or a mixture of one or more of them with a sparingly soluble alkyl ketal ester such as propyl-LGK, ethyl-LPK, ethyl-LEK and the like.

Formulations in which the alkyl ketal ester is present in an oil phase (such as to dissolve or compatibilize components within an oil phase) can contain a partially or fully water-miscible alkyl ketal ester, a sparingly soluble alkyl ketal ester such as propyl-LGK, ethyl-LPK, n-butyl-LPK, ethyl-LEK and the like, or a mixture of one or more of a sparingly water-miscible alkyl ketal ester with a partially- or fully-water miscible alkyl ketal ester.

Waxy formulations such as lip balms or other hydrophobic formulations in which the alkyl ketal ester is called upon to compatibilize water or another polar compound, such as glycerol, into the formulation typically include a fully water-miscible of alkyl ketal ester such as methyl-LGK, ethyl-LGK, methyl-AcAcGK, or partially water-miscible type, but can also include a sparingly-miscible type.

Many personal care formulations are combinations of two or more of the foregoing formulation forms. For example, some personal care formulations contain an aqueous phase that contains a dissolved active agent, and further includes an oil phase which can be present, for example, to supply emollients and/or humectants, or to produce a specific formulation form (cream, lotion and the like). In such cases, it is possible to include two or more alkyl ketal esters within the formulation to perform different functions. Thus, for example, a fully-water-miscible alkyl ketal ester might be present in the aqueous phase to help dissolve the active agent, and a partially- or sparingly water-miscible alkyl ketal ester might be present within the oil phase to reduce its viscosity or compatibilize its components. Either of these alkyl ketal esters can also perform some emulsifying or compatibilizing function between the aqueous and oil phases.

In addition, a single alkyl ketal ester can perform multiple functions within a personal care formulation, such as dissolving an active agent into an aqueous or oil phase, compatibilizing or emulsifying an aqueous phase with an oil phase, etc.

The alkyl ketal ester can reside in an aqueous phase, in an alcoholic or alcohol-water phase, or in an oil phase of a personal care formulation, depending on the particular formulation and the particular alkyl ketal ester. In many cases, an alkyl ketal ester can become distributed between aqueous and oil phases of a personal care formulation, due to its solubility in both phases. In some cases, the alkyl ketal ester can reside at the boundary of aqueous and oil phases.

The amount of alkyl ketal ester present in a personal care formulation depends on the function of the alkyl ketal ester, the other ingredients of the personal care formulation, the specific form of the personal care formulation, and like considerations. In general, the formulation comprises 0.001 to 90%, 0.01 to 80%, 0.1 to 70%, or 0.1 to 50% by weight of the alkyl ketal ester based on the total weight of the formulation, although a more typical amount is from 0.5 to 25% by weight, and in many cases from 1 to 10% by weight of the total formulation weight.

Anti-aging, anti-acne, skin whitening and sun protection formulations can contain 0.001 to 50% of the active agent, specifically from 0.01 to 40% by weight, based on the total weight of the formulation. Anti-aging and anti-acne formulations typically are formulated into aqueous and/or ethanolic solutions, or into lotions or creams. Sun protection formulations can take the form of clear, low viscosity liquids (as is typical for spray-on formulations, which are often ethanolic or ethanol-water based), or else are lotions or creams. Spray-on sun protection formulations typically are aqueous and/or ethanolic solutions or dilute emulsions. Many of the anti-aging, anti-acne, skin whitening and sun protection active agents are soluble to the extent of at least 5 parts per 95 parts of the alkyl ketal ester in the formulation. These include, for example, avobenzone, coenzyme Q10, hydroquinone, oxybenzone, and salicylic acid, all of which are soluble to the extent of at least 5 parts per 95 part of ethyl-LGK, ethyl-LPK, n-Bu-LGK, or a combination thereof. In these cases, the presence of the alkyl ketal ester often allows the amount of ethanol to be reduced, and/or the amount of active agent to be increased at a constant ethanol content, leading to a formulation which is less drying to the skin. In some cases, the ketal may be used to replace a heavy-feeling material that solubilizes the active. Some of these active agents, such as benzoyl peroxide, resveratrol, glycolic acid, and retinoic acid, tend to have lower solubilities in many alkyl ketal esters, such as ethyl-LGK and ethyl-LPK. In those cases the alkyl ketal ester can have less of a solubilizing function and can instead (or in addition) function to improve the feel of the formulation or to compatibilize other materials, such as emollients, into the formulation. In many cases, the usage level of the active is well within the solubility range of the active in the ketal, even at the low solubility end. Retinoic acid, for instance, is commonly used at 0.2% or less in the formulation.

An anti-aging, anti-acne, skin whitening, or sun protection formulation can contain additional UV absorbing agents, notably inorganic compounds such as titanium dioxide or zinc oxide. These materials are solid particles that typically are dispersed into a lotion or cream formulation.

Sun protection formulations such as sunscreens often contain a mixture of organic UV absorbing agents, often in order to broaden the range of wavelengths of UV light that are absorbed. Such mixture of organic UV agents can include two or more of avobenzone, octylmethoxyl cinnamate, oxybenzone, and ethylhexyl salicylate. These may, in the aggregate, constitute from 0.1 to 50% of the weight of the sunscreen formulation, and more preferably constitute from 2 to 25% by weight thereof.

A tanning formulation typically contains from 1 to 25%, preferably from 2 to 10% by weight of one or more tanning agents as described before. Tanning formulations often are formulated into a lotion or a cream. Spray-on tanning formulations are typically aqueous and/or ethanolic solutions.

A tanning formulation can contain organic UV active agents, as described before, as well as inorganic UV active agents such as titanium dioxide or zinc oxide. As is the case with sunscreen formulations, organic UV active agents can constitute from 0.1 to 50%, specifically 0.1 to 30% of the weight of a tanning formulation, and more specifically from 2 to 25% by weight thereof. A mixture of organic UV additives can be present, including a mixture of two or more of avobenzone, octylmethoxyl cinnimate, oxybenzone, and ethylhexyl salicylate.

Anti-dandruff formulations typically contain from 0.1 to 25%, specifically from 0.5 to 10% by weight of one or more of an anti-fungal agent as described before. The formulation form is typically an aqueous solution, aqueous gel, or dilute emulsion containing mostly aqueous phase. An anti-dandruff formulation typically contains one or more surfactants, particularly one or more anionic surfactants. Sulfosuccinate, lauryl sulfate, and laureth sulfate surfactants and the various fatty acid betaines, or fatty acid amide propyl betaines are preferred types, although others, particularly other anionic surfactants, can be used. Surfactants can constitute from 0.1 to 10% by weight of an anti-dandruff formulation. The surfactants can function as cleaning agents and/or emulsifiers in the formulation. An anti-dandruff agent can contain hair conditioners and other materials as well.

Anti-alopecia formulations typically contain from 0.1 to 25%, preferably from 1 to 10% of one or more of anti-alopecia agents. Formulations of these types typically are formulated into low to medium viscosity fluids, which can contain a propellant and be sprayable, which can be clear solutions in the case of anti-alopecia formulations or opaque emulsions in the case of anti-dandruff formulations. These formulations often contain propylene glycol, ethanol, and/or water as a cosolvent mixture, although an advantage of this invention is that levels of propylene glycol and/or ethanol can in some cases be reduced due to the presence of the alkyl ketal ester.

Chemical treatment formulations for hair include hair straighteners, relaxers, and/permanent wave formulations can contain one or more materials which straighten hair, possibly by breaking sulfur-sulfur bonds in keratin or some other component of hair; among these are the depilatory agents described before. They typically constitute up to 10% by weight of a chemical treatment active agent for hair. Chemical treatment formulations for hair can take the form of low viscosity fluids, lotions, creams, or gels.

A hair styling formulation typically will contain one or more hair fixatives, which hold the hair into a re-styled position. The hair fixatives are typically polymeric materials including those indicated under section (g)(1) below. Some of these fixatives can also function as thickeners in a hair straightening and styling formulation. The hair fixative typically constitutes from 0.25 to 25 preferably from 0.5 to 15, weight percent of the formulation. The hair styling formulation can take the form of an aqueous and/or ethanolic solution, a gel, or a lotion.

Anti-perspirant formulations contain one or more anti-perspirant agents such as described before. Anti-perspirant formulations typically take the form of a gel, a viscous liquid (for roll-on applications), or a stick.

A stick or roll-on anti-perspirant typically contains some water, which can constitute from 2 to 60% of the weight of the formulation, and at least 5%, up to 30% by weight of the anti-perspirant agent.

A topical medicinal formulation can contain one or more medicinal agents such as an amphetamine, antihistamine, methylphenidate, oxymetazoline, tetrahydrolzoline hydrochloride, psilocybin, clotrimazole, tea tree oil, piroctone olamine, chlorhexidine, octenidine, triclosan, sodium 3,5-dibromo-4-hydroxybenzenesulfonate (Dibromol), quaternary ammonium salts such as benzalkonium chloride, cetyl trimethylammonium bromide, cetylpyridinium chloride, and benzethonium chloride, and the like. These formulations can be formulated into low viscosity fluids (which can be sprayable), gels, lotions, creams, liniments, or ointments. Low viscosity fluid formulations are typically aqueous and/or ethanolic; lotions and creams are typically emulsions containing an aqueous continuous phase and a dispersed or co-continuous phase that contains an emollient.

Hair dye formulations can include hair dyes such as those described above. Hair bleaching formulations can contain a peroxy-type bleaching agent such as hydrogen peroxide. The dyes and/or bleaches typically constitute from 0.1 to 5% of the total weight of the formulation in the case of dyes; and from 1 to 20% in the case of bleaches. A bleaching formulation can in addition contain an inorganic oxidant such as a persulfate salt, in an amount from 0.1 to 5% by weight. Hair dye and bleaching formulations can take the form of low viscosity fluids, lotions, creams, or gels. They can also be prepared in a water-dilutable concentrate form. A hair dye or bleaching formulation can contain one or more surfactants which can function to stabilize the emulsion, or as a detergent.

Depilatory formulations can contain one or more depilatory agents such as those described before. They typically constitute from 1 up to 20% by weight of a depilatory agent. Depilatory formulations often take the form of lotions, creams, or gels.

In another aspect, and insect repellant formulation comprising an alkyl ketal ester of structure I is provided. An insect repellant formulation can contain insect repellants such as phenoxyethanol, N,N-diethyl-m-toluamide, p-menthane-3,8-diol (active agent in the essential oil of lemon eucalyptus), nepetalactone (catnip oil), citronella oil, permethrin, neem oil, or boy myrtle extract. These can constitute from 0.25 to 50% of the total weight of the insect repellant formulation. Insect repellant formulations often take the form of low viscosity fluids (which can be sprayable), or lotions. A low viscosity insect repellant typically is aqueous and/or ethanolic; water and/or ethanol can constitute up to 98% or more of the weight of such formulations.

In another aspect, a waxy solid formulation that contains a wax, an emollient, and an alkyl ketal ester of structure I is provided. The waxy solid formulation can contain from 0.5 to 20%, 15%, 10%, 8%, 5%, 4%, or 3% by weight water. These formulations can be provided in stick or other solid form. They typically contain at least 20% by weight of an oil such as castor oil, a wax (as defined below) and at least 0.5% by weight of an alkyl ketal ester of structure I. The alkyl ketal ester can be present in an amount up to 25%, 20%, 15%, or 10% by weight of the formulation. The alkyl ketal ester can be a partially or fully water-miscible alkyl ketal ester, as defined below, when the waxy solid formulation contains more than 0.5% by weight water. Such formulations include lip formulations such as a lipstick, lip gloss, or lip balm; cuticle creams; and the like.

Many waxy formulations, including lip care formulations include a mixture of one or more waxes with one or more oils and, in the case of lipsticks, one or more pigments. Lipsticks and lip balm formulations, as well as cuticle creams, tend to be malleable solids at 25° C., whereas lip glosses tend to be viscous liquids or pastes. These formulations are normally characterized as being anhydrous, i.e., containing up to 3% by weight of water. A lip care formulation can contain, for example, from 1 to 30% by weight of a wax; from 30-95% by weight of one or more other hydrophobic materials, of which castor oil is typically an important component; and from 1 to 30% by weight of one or more pigments. In some embodiments, the lipstick or lip balm formulation contains an alkyl ketal ester that is partially or fully miscible with water. In these embodiments, the presence of the alkyl ketal ester allows for some amount of water to be incorporated into the formulations, while retaining other needed properties such as the necessary rheological characteristics (including, in the case of lipsticks in particular, the ability to retain its stick form) and formulation stability. From 0.5 to 10% or more, preferably from 0.5 to 5% by weight water can be incorporated into a lipstick, lip gloss, or lip balm in this manner. The amount of the water-miscible alkyl ketal ester(s) can constitute from 1 to 25% by weight of a waxy formulation such as a lipstick, lip gloss, or lip balm formulation or cuticle cream. In some embodiments, the alkyl ketal ester is present in a part per part by weight water, if water is present.

Similarly, the presence of a partially or fully water-miscible alkyl ketal ester can permit water to be incorporated into other normally anhydrous personal care formulations to the extent of up to 10% or more by weight, without significant change in formulation form or function.

In addition to the foregoing active agent-containing personal care formulations, a significant number of personal care formulations do not contain any of the foregoing active agents, but nonetheless exist in the form of emulsions. The emulsions can be water-in-oil types, oil-in-water types, or types containing co-continuous aqueous and oil phases. These formulations typically take the form of low viscosity fluids (in which the disperse phase, which is typically an oil phase, constitutes a small proportion, typically 35% or less or 10% or less by weight of the formulation), lotions, or creams. These formulations include, for example, hair conditioners, after-shave lotions, various body cleansers, various hand and skin lotions and creams and the like, which do not contain specific active agents as described above. Emulsion formulations of these types typically contain from 0.1 to 50% by weight of an alkyl ketal ester of structure I.

Emulsion formulations, including any of the specific types of formulations described herein that have both an aqueous and an oil phase, such as creams, liniments, lotions, some gels, and mousses, typically contain a component selected from classes (a)-(e) below. In an emulsion, the alkyl ketal ester can reside in the aqueous phase, in the oil phase, in both an aqueous and oil phase, or at the interface between the aqueous and oil phases.

A lotion and a liniment are generally oil-in-water emulsions, but can be water-in oil emulsions. A lotion and a liniment can contain from 0.5 to 25% by weight of one or more materials selected from classes (a)-(e) below. A cream is also generally an oil-in-water emulsion, but can be a water-in-oil emulsion. A cream can contain from 2 to 80% or more of one or more materials selected from classes (a)-(e) below. A cream is an emulsion formulation which is easily deformable but not readily pourable at 25° C.; whereas a lotion is an emulsion formulation which is somewhat viscous (such as having a viscosity of at least 20 cps at 25° C.) but still readily pourable, and used in such a manner. Liniments are of similar viscosity to lotions, but are formulated to be applied using friction. Liniments are often formulated using alcohol, acetone, or similar quickly evaporating solvent. The alkyl ketal esters can advantageously be used to replace some or a portion of these solvents in a liniment.

Mousses are generally colloidal dispersions of a propellant (e.g., a liquid propellant or gas) in a liquid or solid phase. Generally, personal care mousse formulations can contain from 5 to 95% by weight water based on the overall formulation, and can contain from 5 to 95% or more of one or more materials selected from classes (a)-(e) below, wherein an alkyl ketal ester can be substituted for the water or the other materials in amounts from 0.1 to 30% by weight, based on the overall weight of the formulation. The liquid phase can be in solution or emulsion form. In some embodiments, the liquid phase of the mousse is an oil-in-water emulsion wherein water is the continuous phase. Mousses can also be prepared without water where a suitably volatile propellant is in solution with a viscous nonvolatile material containing the alkyl ketal ester.

Other forms for personal care formulations include dispersions, i.e., a combination of a particulate solid in a liquid or thixotropic liquid, for example a paste. A paste is generally a substance that behaves as a solid until a sufficiently large load or stress is applied, at which point it flows like a fluid. Dispersions such as pastes can contain from 1 to 90% by weight of the solid, from 10 to 99% by weight of one or more materials selected from classes (a)-(s) (e.g., petroleum jelly), and from 0.1 to 30% by weight of the alkyl ketal ester in place of the one or more materials (a)-(e).

Still other forms for personal care formulations include ointments, which are generally mineral oil or petrolatum-based formulations that contain no or very little (less than 5% by weight) of water. Ointments can contain from 1 to 99% or more of one or more materials selected from classes (a)-(s) below. Some ointments can contain particles dispersed therein (e.g., zinc oxide) and can therefore also be classified as dispersions.

The personal care formulations can also be in the form of gels, which tend to have a higher viscosity than solutions. The relatively high viscosity can be the result of a thickened solution, or can include, for example, semisolid emulsions in an alcohol base. Gels can contain from 1 to 99% of one or more materials selected from classes (a)-(s) below. Because gels can contain an alcohol base, the alkyl ketal esters can advantageously be used to replace some or a portion of the alcohol.

The personal care formulations can also be in the form of a solution, wherein all of the components are miscible at room temperature as defined above. The solvent can be water, aqueous (containing water and an organic solvent) or organic (e.g., an alcohol). Solutions can contain from 1 to 99% of one or more materials selected from classes (a)-(s) below.

In addition, the personal care formulations can also be in the form of solid, for example, a stick, waxy formulation, or the like. Solids can contain from 1 to 99% of one or more materials selected from classes (a)-(s) below. Solids can also optionally contain particulates. It is to be understood that the foregoing classifications are for convenience only, and that some overlap exists between the forms.

Personal care formulations generally contain additional ingredients, which can be present to perform various functions. Among these are, for example ingredients (a)-(s) as described in more detail below. The various ingredients (a)-(s) can be used alone or in combination. More than one type of each ingredient (e.g., two paraffinic oils (a)) can be used. While certain functions may be ascribed to ingredients (a)-(s), it is to be understood that each ingredient may perform the stated function, another function, or more than one function in a personal care formulation.

Ingredients (a) include paraffinic, naphthenic, or aromatic mineral oil. These materials are often present as all or part of an oil phase in emulsion formulations such as certain lotions and creams. They often function as emollients, by which it is meant a material that tends to soften the skin upon application.

Ingredients (b) included nonionic organic compounds which have a melting temperature of less than 45° C., a molecular weight of at least 190, contain a amido, or ester group and an alkyl chain containing at least 8 carbon atoms, and a solubility in water of no greater than 1 part in 99 parts of water. These include a range of natural oils and synthetic ester and amide formulations which have little or no surfactant properties (having an HLB of less than 4, preferably less than 2) and which often function as emollients in a personal care formulation. These materials are often present as all or part of an oil phase in emulsion formulations such as certain lotions and creams.

Examples of materials (b) include vegetable oils and animal fats and derivatives are useful emollients, including, for example, acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil. Oils which have a required HLB of at least 6, or at least 7, at least 8 or at least 10, tend to dissolve more easily in the alkyl ketal esters and are preferred in cases in which the alkyl ketal ester is to reside at least partially in an oil phase, or in which the alkyl ketal ester is to dissolve or be dissolved into the oil.

Other useful nonionic materials (b) include, for example, $C_{8-24}$ linear or branched alkyl esters of $C_{8-24}$ fatty acids, di-$C_{8-24}$ esters of dicarboxylic acids, $C_{8-24}$ fatty acid esters of $C_{8-24}$ linear or branched alkanoic acids, $C_{8-24}$, especially $C_{12-15}$ alkyl benzoates, poly(propylene oxide) esters of $C_{8-24}$ fatty acids, di-$C_{8-24}$ linear or branched alkyl esters of aromatic diacids, di-$C_{8-24}$ fatty acid esters of aromatic diacids, and the like. Examples of these include cetyl palmitate, cetearyl ethylhexanoate, ethylene glycol distearate, propylene glycol distearate, glycerol distearate, myristyl myristate, lignoceryl erucate, di-PPG-3 myristyl ether adipate, isostearyl neopentanate, ethylhexyl palmitate, dicaprylyl maleate, diisopropyl dimer dilinoleate, dicetylphthalate, ethylhexyl isononanoate, diethyl phthalate, dimethyl phthalate, dibutyl phthalate, triethylene glycol dibenzoate, butyl stearate, disobutyl adipate, and the like.

Other useful materials (b) include, for example, $C_{8-24}$ linear or branched alkyl amides of $C_{8-24}$ fatty acids, di-$C_{8-24}$ amides of dicarboxylic acids, $C_{8-24}$ fatty acid amides of $C_{8-24}$ linear or branched alkanoic acids, poly(propylene oxide) amides of $C_{8-24}$ fatty acids, di-$C_{8-24}$ linear or branched alkyl amides of aromatic diacids, di-$C_{8-24}$ fatty acid amides of aromatic diacids, and the like.

Ingredients (c) include nonionic organosilicone compounds having a melting temperature of less than 45° C. and a solubility in water of no greater than 1 part in 99 parts of water. Examples are dimethicone and cyclopentasiloxane.

Ingredients (d) include long chain (eight or more carbon atoms) alcohols such as 1-octanol, 1-decanol, 1-dodecanol, cetyl alcohol, and the like. These alcohols can perform various functions, including thickening and a solvating/compatibilizing function, and can function as emollients as well.

Ingredients (e) include waxes. In some cases, these waxes perform a skin moisturizing function by depositing onto the skin and forming a barrier to the escape of water from the skin. In other cases, the waxes can function as hair conditioners, or form films upon application (as onto the lips, eyelashes, eyelids, etc.). In still other cases, the wax can provide a personal care formulation with a needed physical form (as is the case with lipsticks and lip balm formulations). Waxes are hydrophobic (having a solubility in water less than 1 part per 99 parts water), solid but malleable at room temperature, and have a melting temperature of from 45 to 100° C. Waxes include synthetic or mineral waxes such as ceresin, montan, ozocerite, peat, paraffin, microcrystalline, polypropylene and other polymerized poly-α-olefin waxes, substituted amide, petroleum jelly, esterified or saponified waxes, and the like; and waxes of plant or animal origin including beeswax, chinese wax, lanolin, shellac wax, spermaceti, bayberry, candelilla, carnauba, castor, esparto, Japan, ouricury, rice bran or soy waxes. Waxes that have a required HLB of at least 6, or at least 7, at least 8 or at least 10, tend to dissolve more easily in the alkyl ketal esters and are preferred in cases in which the alkyl ketal ester is to dissolve or be dissolved into the wax.

Ingredients (f) include liquid or low melting (less than 45° C.) hydrocarbons of various types, which can function as cosolvents, conditioners, propellants, or for other purposes. Examples of these include squalene, butane (all isomers), propane, and pentane (all isomers).

Ingredients (g) include natural, synthetic, or modified organic polymers. Polymers have several primary uses in personal care formulations (some of them being capable of performing multiple functions).

Polymers (g)(1) include hair fixatives. These polymers include polyvinylpyrrolidone; polyvinylpyrrolidone/vinyl acetate copolymers; polyurethane and polyurethane copolymers and blends; copolymers of vinylpyrrolidone, lauryl methacrylate and optionally one or more other acrylate monomers; copolymers of vinyl pyrrolidone and dimethylaminoethyl methacrylate; copolymers of vinyl caprolactam, vinylpyrrolidone and dimethylaminoethyl methacrylate; copolymers of vinyl pyrrolidone and methacrylamidopropyl trimethylammonium chloride; copolymers of vinylpyrrolidone, vinyl caprolactam and dimethylaminopropyl methacrylamide; vinyl acetate/butyl maleate/isobornyl acrylate copolymers; copolymers of isobutylene, ethyl maleimide and hydroxyethyl maleimide; isobutylene/dimethylaminopropyl maleimide/ethoxylated maleimide/maleic acid copolymers; copolymers of poly(vinyl methyl ether) and the ethyl, butyl or isopropyl ester of maleic acid, and the like. These polymers are dissolved or dispersed in solution (usually water, ethanol, a mixture of water and an alcohol) to form hairsprays, mousses, and gels and are often present in amounts up to 20% by weight in hair sprays, styling gels, and similar hair styling formulations. Polymers based on starch or modified starch can also be used as hair fixatives.

Polymers (g)(2) include hair conditioning or skin conditioning polymers. These polymers are used in hair care products and skincare products. They can be either water soluble, oil soluble, or dispersed in water. These include hydrolyzed wheat protein and crosspolymers thereof with polyvinylpyrrolidone; many of the Polyquaternium series such as Polyquaternium-4, -7, -10 and -18 and -28; Polyquaternium-4/hydroxypropyl starch copolymers, PEG-50 hydrogenated palm amide; PPG-14 Palmeth-60 hexyl dicarbamate; cetareth-60 myristyl glycol, and the like.

Polymers (g)(3) include waterproofing polymers. These polymers are dissolved in alcohol or oil phases. They are found in sweat-resistant, water resistant, or rub-resistant formulations for sun care and color cosmetics. These include acrylate polymers and copolymers; polyvinylpyrrolidone and copolymers of vinylpyrrolidone; acrylate/t-octylpropenamide copolymers; polymers and copolymers of polyacrylamide; vinyl acetate/butyl maleate/isobornyl acrylate copolymers; vinyl caprolactam/vinyl pyrrolidone/dimethylaminoethyl methacrylate copolymers; $C_{30-38}$ olefin/isopropyl maleate/maleic acid copolymers; triacontanyl polyvinylpyrrolidone polymers; isobutylene/ethyl maleimide/hydroxylethylmaleimide copolymers; acacia Senegal gum; and various rosins and saccharide polymers. These can constitute up to 20% by weight of a personal care formulation.

Polymers (g)(4) include polymethylmethacrylate, which is useful as a cosmetic additive for a soft focus effect.

Polymers (g)(5) include rheology modifiers. These polymers dissolve in a solution or continuous phase of an emulsion and increase viscosity. Usually, these are water soluble polymers that are added to a water phase. Rheology-modifying polymers include carbomers, natural gums like xanthan gum and guar gum, alkali swellable latexes, hydroxyethyl cellulose, and starch polymers (including modified starches).

Polymers (g)(6) include nitrocellulose, cellulose acetate propionate, cellulose acetate butyrate, styrene/acrylates copolymers, acrylates copolymers, polyethylene terephthalate and tosylamide/formaldehyde resins. These polymers are used in nail lacquer that form the continuous coating used in nail polish.

Ingredients (h) include surfactants. A surfactant includes ionic (cationic, anionic, or zwitterionic) compounds that contain a hydrocarbon group, specifically an alkyl group, of at least 8 carbon atoms. The ionic surfactants include, for example, anionic surfactants which include one or more sulfate, sulfonate or phosphate groups, which are in the neutralized (or "salt") form; cationic surfactants which include one or more quaternary ammonium or quaternary phosphonium groups, which are in the neutralized (or "salt") form; one or more zwitterionic groups which can, depending on the pH of the formulation, assume either an anionic or cationic form (as with the betaines, for example), or can assume a cationic or nonionic form (as with the amine oxide surfactants, for example). A surfactant additionally includes nonionic molecules that have a highly hydrophobic portion and a highly hydrophilic portion. The nonionic surfactants are characterized as having an HLB of at least 4, preferably from 6 to 22. A detailed listing of suitable surfactants can be found McCutcheon's EMULSIFIERS AND DETERGENTS, North American Edition, 1984, McCutcheon Division, MC Publishing Company, incorporated herein by reference.

Specific anionic surfactants include alkyl benzene sulfonates, including C11-16 alkyl benzene sulfonates, alkyl- and alkylether sulfates such as sodium dodecyl sulfate, sodium laureth sulfate, ammonium lauryl sulfate and sodium lauryl ether sulfate; taurates (anionic acylamino alkane surfactants); paraffin sulfonates including C12-18 paraffinsulfonates, olefin sulfonates, alpha-sulfonates of fatty acids and of fatty acid esters, sulfosuccinate salts, ammonium cocoyl isethionate, ammonium laureth sulfate, ammonium lauryl sulfate, cocoyl sarcosine, diethylhexyl sodium sulfosuccinate, disodium cocamido MEA sulfosuccinate, disodium cocamido MIPA sulfosuccinate, disodium laureth sulfosuccinate, disodium lauryl sulfosuccinate, disodium oleamido MEA sulfosuccinate, disodium oleamido MIPA sulfosuccinate, disodium oleamido PEG-2 sulfosuccinate, sodium polystyrene sulfonate, and lauroyl sarcosine. The anionic surfactants can be used in the form of their sodium, potassium, or triethanolammonium salts.

Specific nonionic surfactants include alkoxylated (especially ethoxylated) alcohols and alkyl phenols, alkyl polyglucosides such as octyl glucoside, decyl maltoside, isethionates, amides of long chain fatty acids such as cocamide MEA, cocamide DEA, cocamide TEA and polyethoxylated tallow amine, and lauramide surfactants; various amine oxides, alkyl betaines; poly(ethylene oxide)-poly(propylene oxide) copolymers PEG-5 soyamine, PG-hydroxyethyl cellulose stearyldimonium chloride, quaternium-91 & PPG-3 benzyl ether myristate, PEG-50 hydrogenated palm amide capramide DEA, cocamide MIPA, PEG stearates, PEG ditallate, PEG cocamines, PEG soyamines, PEG stearamines, PEG tallowamines, and the like. Organosilicone surfactants are also useful nonionic surfactants.

Specific cationic surfactants include such as cetylpyridium chloride, benzalkonium chloride, benzethonium chloride Quatenrium-82, dicetyldimonium chloride, dipalmitoylethyldimonium chloride, soytrimonium chloride, Celquat H-100 (cationic cellulose polymer), hydroxyoctacosanyl hydroxylstearate, behentrimonium methosulfate, cetrimonium chloride, and the like. These often function as antimicrobials and antistatic agents in a personal care formulation.

Specific zwitterionic types of surfactants include dodecyl betaine, dodecyl dimethylamine oxide; such as, alkyl polyglucosides, disodium lauroamphodiacetate, disodium cocoamphodiacetate, sodium lauroamphoacetate, disodium capryloamphodiacetate, sodium amphocarboxylate, sodium cocoamphoacetate, sodium cocoamphopropionate, stearamine oxide, cetyl betaine, cocamidopropyl betaine, babassuamidopropyl betaine, cocamidopropyl hydroxysultaine, cocamidopropylamine oxide, cocamine oxide, cocaminopropionic acid, coco-betaine, coco/sunfloweramidopropyl betaine, dihydroxyethyl tallowamine oxide, disodium caprylamphodiacetate, disodium cocoamphodiacetate, disodium cocoamphodipropionate, disodium lauroamphodiacetate, disodium soyamphodiacetate, disodium wheatgermamphodiacetate, hydrogenated tallowamine oxide, lauramidopropyl betaine, lauramidopropylamine oxide, lauramine oxide, lauryl betaine, laurylhydroxylsultaine, oleyl betaine, palmitamine oxide, potassium dihydroxyethyl cocaminopropylamine oxide, sodium cocoa butteramphoacetate, sodium cocoamphoacetate, sodium cocoamphopropionate, sodium lauraphoacetate, sodium lauriminodipropionate, stearamine oxide, wheat germamidopropyl betaine, and the like.

Ingredients (i) include natural or synthetic fragrances, including for example, citrus floral herbal, citrus floral tea, citrus woody, coconut mango, desert flower, dewy morning, eau glacier, floral dove, fresh mint, green aromatic, lemongrass green tea, orange blossom honey, orange mimosa, tropical sunset, vanilla floral musk, vanilla grapefruit, white rose, white tea, menthol, and the like.

Ingredients (j) include botanical extracts such as white tea extract, soy isoflavone extract, red clover extract, passion flower extract, olive extract, green tea extract, grape extract, ginseng extract, chamomile extract, centella asiatica extract, balm mint extract, aloe barbadensis leaf extract, rosemary extract, dulse seaweed extract, acacia extract, acai extract, agave extract, alfalfa extract, almond extract, angelica extract, annatto extract, apple extract, apricot extract, arnica extract, ashwagendha extract, awapuhi extract, bamboo extract, banana extract, basil extract, bearberry extract, beet root extract, bergamot extract, bilberry extract, bitter orange extract, black current extract, black pepper extract, black tea extract, bladderwrack extract, brazil nut extract, buchu extract, burdock extract, butchers broom extract, calendula extract, camu extract, capsicum extract, cardamom extract, carrot extract, cats claw extract, caviar extract, chia extract, chickory extract, cinnamon extract, cocoa extract, coconut extract, coffee extract, coltsfoot extract, comfrey extract, cotton extract, cranberry extract, cucumber extract, daisy extract, dandelion extract, Echinacea extract, elder extract, elderberry extract, eucalyptus extract, fenugreek extract, fig extract, flax extract, fo-ti extract, frangipani extract, frankincense extract, ginger extract, ginkgo biloba extract, goji berry extract, goldenseal extract, grapefruit extract, guarana extract, guava extract, hawthorn extract, heal all extract, heather extract, henna extract, hibiscus extract, honey extract, hops extract, horse chestnut extract, horseradish extract, horsetail extract, irish moss extract, ivy extract, jasmine extract, jatoba extract, jojoba extract, jujube extract, kelp giant extract, kiwi extract, kiwi berry extract, lavender extract, lemon extract, lemon balm extract, lemongrass extract, licorice extract, lime extract, linden flower extract, lotus flower extract, luo han guo extract, madder root extract, mallow extract, mandarin orange extract, mango extract, mangosteen extract, marjoram extract, marshmallow extract, milk thistle extract, neem extract, nettle extract, noni extract, oat extract, olive leaf extract, oolong tea extract, orange flower extract, orchid extract, papaya extract, paper mulberry extract, parsley extract, pear extract, peony extract, peppermint extract, perilla extract, pineapple extract, pomegranate extract, pumpkin extract, queen of the meadow extract, quillaia extract, quince extract, raspberry extract, reishi extract, rooibos extract, rose extract, sage extract, sandalwood extract, saw palmetto extract, sea buckthorn extract, silk tree extract, spirulina extract, St. John's wort extract, strawberry extract, suma extract, sunflower extract, tangerine extract, tea tree extract, thyme extract, tiare extract, valerian root extract, vanilla extract, walnut black extract, watercress extract, white lily extract, white peony tea extract, white willow extract, witch hazel extract, yarrow extract, yerba mate extract, yogurt extract, yohimbe extract, yucca extract, and the like. These extracts can be present for fragrance purposes, or as specific active agents in particular formulations.

Ingredients (k) include natural or synthetic dyes such as quinolines (D&C Yellow 10 and 11), triphenylmethanes (FD&C Blue 1, Green 3 and D&C Blue 4), anthraquinones (D&C Green 5,6 and Violet 2), indigoids (D&C Red 30), Non-azo xanthene (fluoran), xanthenes (D&C Red 22 & Yellow 8), fluorans (D&C Red 21, 27, and Orange 5), D&C Red 36, FD&C Yellow 5, FD&C Yellow 6, D&C Red 33, D&C Red 40, D&C Orange 4, D&C Red No. 6, D&C Red 7, D&C Red 34, sericite, D&C Yellow 10, henna (black, brown, gold brown, mahogany), and the like.

Ingredients (l) include inorganic pigments or pearlizers such as white mica, lead pearl, natural pearlessence, bismuth oxychloride, oxide coated mica ((OCM), titanium dioxide, ferric(III) oxide, aluminum, silica, borosilicate, synthetic mica, mica spheres, titanium, barium sulfate, hectorite, ferric (ammonium) ferrocyanide, cadmium yellow, cadmium red, cadmium green, cadmium orange, carbon black, ivory black, chrome yellow, chrome green, cobalt violet, cobalt blue, cerulean blue, aureolin (cobalt yellow), Han purple, Egyptian blue, Paris green, verdigris, viridian, sanguine, caput mortuum, iron oxide red, red ochre, Venetian red, Prussian blue, yellow ochre, raw sienna, burnt sienna, raw umber, burnt umber, lead white, cremnitz white, Naples yellow, red lead, vermilion, titanium yellow, titanium beige, titanium oxide, titanium black, ultramarine, ultramarine green, and the like.

Ingredients (m) include lower alcohols, including $C_{1-7}$ alkanols such as ethanol, 1-propanol, 2-propanol, 1-butanol, 2-butanol, t-butanol, 1-pentanol, 1-hexanol, as well as the various other isomers of pentanol and hexanol; alkylene glycols such as ethylene glycol, diethylene glycol, triethylene glycol, 1,2-propylene glycol, 1,3-propane diol, dipropylene glycol, tripropylene glycol 1,4-butane diol and 1,2-butane diol; triols such as glycerine, and the like. These can function as solvents or cosolvents, or as humectants in personal care formulations.

Ingredients (n) include glycol ethers, which can function as solvents or cosolvents or but in some cases can perform other functions. Examples of these glycol ethers include ethylene glycol monomethyl ether, ethylene glycol monoethyl ether, propylene glycol monomethyl ether, propylene glycol monoethyl ether, diethylene glycol monomethyl ether, diethylene glycol monoethyl ether, diethylene glycol mono-n-butyl ether, dipropylene glycol monoethyl ether, dipropylene glycol monobutyl ether, dipropylene glycol monohexyl ether, propylene glycol monobutyl ether, diethylene glycol monohexyl ether, and the like.

Ingredients (o) include active pH adjusters/buffers and chelating agents including 2-amino-2-methyl-1-propanol, 2-amino-1-methyl-1,3-propanediol, tris(hydroxymethyl) aminomethane, alpha-hydroxy acids such as lactic acid and glycolic acid), citric acid, citric acid salts, phosphoric acid salts, ascorbic acid salts, triethanolamine, sodium hydroxide, aminomethyl propanol, potassium hydroxide, diethanolamine, sodium carbonate, potassium hydrogen tartrate, levulinic acid, and the like. It is preferred to buffer a personal care formulation containing an alkyl ketal ester to a pH of at least 3.5, especially when the personal care formulation contains a sulfonate or sulfate surfactant, or other sulfonic acid or sulfate salt. A pH from 5 to 8 can be used in aqueous formulations.

Ingredients (p) include organic carboxylic acids having from 2 to 10 carbon atoms.

Ingredients (q) include inorganic particulates such as clays, magnesium aluminum silicate, magnesium trisilicate, attapulgite, bentonite, hectorite, lithium magnesium silicate, lithium magnesium sodium silicate, montmorillonite, bentonite, smectite clay, boron nitride, silicon nitride, titanium carbide, boron carbide, mullite, coreiderite, and the like.

Ingredients (r) include non-hydrocarbon propellants such as hydrofluorocarbon 152A, nitrogen, 1,2-trichlorotrifluoroethane, chloropentafluoroethane, dimethyl ether, and the like.

Ingredients (s) include preservatives such as diazolidinyl urea, methyl paraban, propyl paraban, and mixed paraban esters, and the like.

Formulations containing an alkyl ketal ester, especially a sparingly water-soluble alkyl ketal ester, have been found to be excellent cosmetic removers, particularly if the formulation contains at least 5% and more specifically at least 8% by weight of the alkyl ketal ester. The alkyl ketal ester can constitute up to 75%, up to 60% or up to 50% of the weight of a cosmetic remover formulation. A cosmetic remover in accordance with the invention can include, in addition to the alkyl ketal ester, water, an alcohol such as ethanol, isopropanol or 1,2- or 1,3-propane diol; one or more of components (a)-(e) above (in which case the cosmetic remover will tend to be in the form of an emulsion which can be in lotion or cream form), or any of the other materials (f)-(s) above. Such a cosmetic remover can even be free of surfactants, or contain low (less than 2% by weight) concentrations of surfactants.

The alkyl ketal esters are also efficient solvents for polymers that are generally present in nail polishes, such as nitrocellulose, cellulose acetate propionate, cellulose acetate butyrate, styrene/acrylates copolymers, acrylates copolymers, polyethylene terephthalate and tosylamide/formaldehyde resins and thus find benefit as solvents in nail polish removers, nail strengthening formulations, and/or nail polishes.

The personal care formulations described herein satisfy certain continuing needs in the art for formulary ingredients. The alkyl ketal esters can be used in a wide range of formulation forms and in a wide variety of specialized applications. Although these various types of formulations differ enormously, as do the conditions under which they are used, the alkyl ketal esters can be used in the formulation of many of them, which greatly simplifies the formulation process.

In addition, formulators of personal care formulations must often simultaneously address formulation needs that are often competing and sometimes even contradictory. For example, many personal care formulations contain an active agent that lends a particular functional attribute to the formulation. It can be desirable to increase the concentration of the active agent in a given formulation, or to produce a formulation that contains the active agent in a specific formulation form (such as a solution, dispersion, lotion, cream, stick, gel, or the like), but the formulator is limited by the solubility of the active agent in the other ingredients in the formulation. Approaches to address solubility include the use of various types of emulsifiers, oils, cosolvents, and the like, but it is often the case that other requirements, such as the specific formulation form, are incompatible with the presence of such materials in the amounts needed for efficacy. Use of the alkyl ketal esters allows an increased concentration of active agent in a wide variety of specific personal care formulation forms. The alkyl ketal esters are further compatible with many other ingredients of personal care formulations.

In other cases, the presence or absence of a specific ingredient that can be an aid to solubility is important. For example it can be desirable to reduce or eliminate volatile organic compounds ("VOCs") from a personal care formulation, in favor of an aqueous-based formulation. Some ingredients, such as ethanol, can dry the skin and in some cases are to be avoided for that reason, or for other reasons, such as VOC regulations in some jurisdictions. Conversely, there are other cases in which ethanol and/or another relatively volatile material is desired, so the formulation dries rapidly when it is applied, for example. In some embodiments, use of the alkyl ketal esters results in formulations that do not contain VOCs. In an embodiment, the formulations and products described herein can be low-VOC as defined below.

Use of the alkyl ketal esters in personal care formulations can enhance the compatibility amongst the various ingredients of the formulations. Many personal care formulation formulations contain both hydrophilic and hydrophobic components. These ingredients tend not to mix into each other. In order to create a formulation that does not rapidly separate into oil-rich and water-rich layers, emulsifiers, cosolvents, or thickeners can be included so that it becomes kinematically stable. These emulsifiers, cosolvents, and thickeners often play little role in the function or performance of the formulation (i.e., are not active agents), although they can affect the spreading characteristics and feel on the skin. They mainly are present to permit the various functional ingredients to coexist in a stable formulation form or to provide a desired feel or consistency to the formulation. The inclusion of certain compatibilizing ingredients (such as volatile or drying organic solvents, for example), as described above, can more preferably be omitted from some formulations. The need to include such compatibilizers can increase formulation complexity. Formulations that require compatibilization can be very sensitive to small formulational changes. Small changes to a formulation often destabilize it, requiring a new balance of ingredients.

The alkyl ketal esters can perform the function of emulsifiers, oils, cosolvents, compatibilizers, and like materials. In a further advantage, the alkyl ketal esters enhance the spreading of the formulation, and/or do not feel greasy or heavy. Use of the alkyl ketal esters can provide simplified formulations for personal care formulations that still have the needed formulation attributes and functions. In other cases, use of the alkyl ketal esters can reduce the quantities of the various formulary components, and thus can reduce costs and simplify formulating. This can allow a formulator to maintain a simplified raw material inventory and thus reduce associated costs. Use of the alkyl ketal esters can also result in personal care formulation formulations that are more robust to formulation changes.

The following examples are provided to illustrate the invention but are not intended to limit the scope thereof. All parts and percentages are by weight unless otherwise indicated.

EXAMPLES

Examples 1-6 show the effect of the alkyl ketal esters on solubility of various personal care formulation ingredients. In these tests, clear mixtures as observed without magnification from a distance of, e.g., 0.3 meters are considered to be "miscible," whereas cloudy or phase separated mixtures are considered to be "immiscible."

Example 1

Model Ethanolic Avobenzone Sunscreen Solutions

Three-component mixtures of ethyl-LPK, ethanol, and avobenzone were prepared by mixing the materials at various proportions at room temperature in a vial and shaking. Avobenzone by itself is immiscible in ethanol at the 5% by weight level. Results are shown in Table 1.

TABLE 1

| Result | % avobenzone | % Et-LPK | % ethanol |
|---|---|---|---|
| Miscible | 2.0 | 0.0 | 98.0 |
| Cloudy/Immiscible | 5.0 | 0.0 | 95.0 |
| Miscible | 7.4 | 22.3 | 70.3 |
| Miscible | 10.6 | 31.8 | 57.6 |
| Miscible | 13.1 | 39.3 | 47.6 |
| Miscible | 16.2 | 48.6 | 35.1 |
| Miscible | 18.1 | 54.2 | 27.8 |
| Miscible | 27.1 | 63.3 | 9.5 |

These data show that avobenzone concentrations as high as 27% can be achieved in an ethanolic solution through the addition of ethyl-LPK as a cosolvent. Thus, higher concentrations of this UV agent can be provided in a formulation that is suitable for use in a spray-on sunscreen formulation.

Three-component mixtures of ethyl-LGK, ethanol, and avobenzone were prepared by mixing the materials at various proportions at room temperature in a vial and shaking. Results are shown in Table 2.

TABLE 2

| Result | % avobenzone | % Et-LGK | % ethanol |
|---|---|---|---|
| Miscible | 2.0 | 0.0 | 98.0 |
| Cloudy/Immiscible | 5.0 | 0.0 | 95.0 |
| Miscible | 6.9 | 42.1 | 51.0 |
| Miscible | 8.5 | 52.1 | 39.4 |
| Miscible | 10.9 | 67.0 | 22.1 |
| Miscible | 12.0 | 74.0 | 13.9 |

These data show that avobenzone concentrations as high as 12% can be achieved in an ethanolic solution through the addition of ethyl-LGK as a cosolvent. Again, the presence of the alkyl ketal ester allows higher concentrations of this UV agent to be provided in a formulation that can be suitable for use in a spray-on sunscreen formulation.

Example 2

Model Ethanolic and Aqueous Oxybenzone Sunscreen Solutions

Three-component mixtures of ethyl-LPK, ethanol, and oxybenzone were prepared by mixing the materials at various proportions at room temperature in a vial and shaking. Clear mixtures were considered to be "miscible" on this test, whereas cloudy or phase separated mixtures were considered to be "immiscible." Oxybenzone by itself is immiscible in ethanol at the 10% by weight level. Results are shown in Table 3A.

TABLE 3A

| Result | % Oxybenzone | % Et-LPK | % ethanol |
|---|---|---|---|
| Miscible | 6.5 | 0.0 | 93.5 |
| Cloudy/Immiscible | 10.0 | 0.0 | 90.0 |
| Miscible | 11.7 | 21.7 | 66.6 |
| Miscible | 14.7 | 34.2 | 51.1 |
| Miscible | 18.3 | 34.0 | 47.8 |
| Miscible | 28.2 | 65.8 | 6.0 |

These data show that oxybenzone concentrations as high as 28% can be achieved in an ethanolic solution through the addition of ethyl-LPK as a cosolvent. Thus, higher concentrations of this UV agent can be provided in a formulation that was suitable as a spray-on sunscreen formulation.

A similar set of experiments was run, replacing ethyl-LPK with ethyl-LGK. This time, up to 17% of the active can be incorporated into an ethanolic solution as shown in Table 3B.

TABLE 3B

| Result | % Oxybenzone | % Et-LGK | % ethanol |
|---|---|---|---|
| Miscible | 6.5 | 0.0 | 93.5 |
| Cloudy/Immiscible | 10.0 | 0.0 | 90.0 |
| Miscible | 11.1 | 50.6 | 38.3 |
| Miscible | 12.8 | 58.3 | 28.9 |
| Miscible | 14.1 | 64.1 | 21.9 |
| Miscible | 15.3 | 69.5 | 15.3 |
| Miscible | 16.6 | 75.8 | 7.6 |

These data show that oxybenzone concentrations as high as 17% can be achieved in an ethanolic solution by the addition of Et-LGK as a cosolvent. Thus, higher concentrations of this UV agent can be provided in a formulation that can be suitable for use in a spray-on sunscreen product.

A third set of experiments was run, this time replacing ethyl-LPK with ethyl-LEK. This time, up to 30% of the active can be incorporated into an ethanolic solution, as shown in Table 3C.

TABLE 3C

| Result | % oxybenzone | % Et-LEK | % ethanol |
|---|---|---|---|
| Miscible | 6.5 | 0.0 | 93.5 |
| Cloudy/Immiscible | 10.0 | 0.0 | 90.0 |
| Miscible | 12.2 | 22.6 | 65.3 |
| Miscible | 14.8 | 27.6 | 57.6 |
| Miscible | 17.4 | 32.3 | 50.2 |
| Miscible | 21.4 | 39.8 | 38.8 |
| Miscible | 25.1 | 46.7 | 28.2 |
| Miscible | 30.8 | 57.2 | 12.0 |

These data show that oxybenzone concentrations as high as 30% can be achieved in an ethanolic solution by the addition of Et-LEK as a cosolvent. Thus, higher concentrations of this UV agent can be provided in a formulation that can be suitable in a spray-on sunscreen product.

A fourth set of experiments was run, this time replacing ethyl-LEK with propyl-LGK as shown in Table 3D.

TABLE 3D

| Result | % oxybenzone | % propyl-LGK | % ethanol |
|---|---|---|---|
| Miscible | 10.0 | 90.0 | 0 |
| Miscible | 9.3 | 83.6 | 7.1 |
| Miscible | 6.7 | 59.9 | 33.4 |
| Miscible | 4.7 | 42.4 | 52.9 |
| Miscible | 3.5 | 31.6 | 64.9 |
| Miscible | 3.0 | 27.3 | 69.7 |
| Miscible | 6.5 | 0.0 | 93.5 |
| Cloudy/Immiscible | 10.0 | 0.0 | 90.0 |
| Miscible | 11.96 | 88.04 | 0 |
| Cloudy/Immiscible | 17.83 | 82.17 | 0 |

These data show that the window of solubility is only slightly enhanced since the stock concentration of oxybenzone in propyl-LGK (10% based on maximum solubility of 10-18%) is only slightly larger than the upper limit of oxybenzone solubility in ethanol (6.5-10%).

Three-component mixtures of Et-AcAc-GK, water, and oxybenzone were prepared to show that the acetoacetate analog has a region where it couples to oxybenzone into water. Results are shown in Table 4A.

TABLE 4A

| Result | % oxybenzone | % Et-AcAc-GK | % water |
|---|---|---|---|
| Cloudy/Immiscible | 1.0 | 0 | 99.0 |
| Miscible | 0 | 50.0 | 50.0 |
| Miscible | 18.0 | 82.0 | 0.0 |
| Cloudy/Immiscible | 17.1 | 78.1 | 4.8 |
| Cloudy/Immiscible | 16.7 | 76.2 | 7.1 |
| Miscible | 9.8 | 90.2 | 0 |
| Miscible | 9.6 | 88.5 | 2.0 |
| Miscible | 9.3 | 86.1 | 4.6 |
| Miscible | 9.1 | 84.2 | 6.7 |
| Miscible | 8.9 | 81.8 | 9.4 |
| Miscible | 8.7 | 80.3 | 11.0 |
| Miscible | 8.5 | 78.8 | 12.7 |
| Miscible | 8.4 | 77.2 | 14.4 |
| Miscible | 8.1 | 74.9 | 17.0 |
| Cloudy/Immiscible | 7.9 | 72.5 | 19.6 |
| Cloudy/Immiscible | 2.0 | 0 | 98.0 |
| Miscible | 25.0 | 75.0 | 0 |
| Cloudy/Immiscible | 22.7 | 68.1 | 9.3 |
| Cloudy/Immiscible | 24.0 | 72.0 | 4.0 |
| Cloudy/Immiscible | 31.9 | 68.1 | 0 |
| Miscible | 29.0 | 71.0 | 0 |

These data show that oxybenzone concentrations as high as 29% can be achieved in a solution through the addition of Et-AcAc-GK as a cosolvent. Thus, higher concentrations of this UV agent can be provided in a formulation that can be suitable for use in a spray-on sunscreen product.

In a second experiment, three-component mixtures of oxybenzone with water and methyl-LGK were made. Methyl-LGK and water are miscible at 50/50. Results are shown in Table 4B.

TABLE 4B

| Result | % oxybenzone | % Methyl-LGK | % water |
|---|---|---|---|
| Miscible | 10.0 | 90.0 | 0 |
| Miscible | 9.7 | 86.9 | 3.5 |
| Miscible | 9.1 | 81.5 | 9.4 |
| Miscible | 8.7 | 78.5 | 12.7 |
| Miscible | 8.3 | 75.1 | 16.5 |
| Cloudy/Immiscible | 8.7 | 70.5 | 21.6 |
| Miscible | 0 | 50.0 | 50.0 |
| Cloudy/Immiscible | 1.0 | 0 | 99.0 |

These data show that oxybenzone concentrations as high as 10% can be achieved in a solution through the addition of Methyl-LGK as a cosolvent. Thus, higher concentrations of this UV agent can be provided in a formulation that can be suitable in a spray-on sunscreen product.

A third set of experiments was run, this time replacing methyl-LGK with mixed ketals where one is soluble in water and one is with limited solubility (Et-LGK and Et-LPK (here at 80/20 weight ratio). Results are shown in Table 4C.

TABLE 4C

| Result | % oxybenzone | % ketal solvent mixture | % water |
| --- | --- | --- | --- |
| Cloudy/Immiscible | 1.0 | 0 | 99.0 |
| Miscible | 20.0 | 80.0 | 0 |
| Miscible | 19.5 | 77.8 | 2.7 |
| Miscible | 18.9 | 75.5 | 5.6 |
| Miscible | 18.3 | 73.3 | 8.3 |
| Cloudy/Immiscible | 18.0 | 71.9 | 10.1 |
| Miscible | 10.0 | 90.0 | 0 |
| Miscible | 9.7 | 87.5 | 2.8 |
| Miscible | 8.7 | 78.7 | 12.6 |
| Miscible | 8.6 | 77.0 | 14.5 |
| Cloudy/Immiscible | 8.3 | 75.0 | 16.7 |

The results in Table 4C shows that a mixed system of Et-LGK and Et-LPK (here at 80/20 weight ratio) can also couple oxybenzone into water, even though the water tolerance of Et-LPK is low. The addition of Et-LPK narrows the miscibility window compared to Et-LGK alone; nonetheless, the system works. These data show that oxybenzone concentrations as high as 20% can be achieved in a solution through the addition of an alkyl ketal solvent mixture as a cosolvent. Thus, higher concentrations of this UV agent can be provided in a formulation that was suitable as a spray-on sunscreen formulation.

Three-component mixtures of ethyl-LGK, water, and oxybenzone were prepared by mixing the materials at various proportions at room temperature in a vial and shaking. Clear mixtures were considered to be "miscible" on this test, whereas cloudy or phase separated mixtures were considered to be "immiscible." Oxybenzone by itself is immiscible in water at 1% by weight. Results are shown in Table 4D.

TABLE 4D

| Result | % Oxybenzone | % Et-LGK | % water |
| --- | --- | --- | --- |
| Miscible | 10 | 80 | 10 |
| Miscible | 10 | 75 | 15 |
| Miscible | 5 | 70 | 25 |
| Miscible | 13.5 | 76.7 | 9.7 |
| Miscible | 12.8 | 72.8 | 14.4 |
| Miscible | 11.8 | 66.8 | 21.4 |
| Cloudy/Immiscible | 11.1 | 63.0 | 25.9 |
| Miscible | 16.6 | 75.8 | 7.6 |
| Cloudy/Immiscible | 15.8 | 72.1 | 12.1 |
| Cloudy/Immiscible | 16.4 | 74.5 | 9.1 |
| Miscible | 4.1 | 78.6 | 17.2 |
| Miscible | 3.8 | 72.5 | 23.7 |
| Miscible | 3.5 | 67.3 | 29.2 |
| Miscible | 3.3 | 62.3 | 34.4 |
| Miscible | 3.1 | 58.1 | 38.9 |
| Miscible | 3.0 | 56.3 | 40.7 |
| Cloudy/Immiscible | 2.7 | 50.9 | 46.5 |
| Cloudy/Immiscible | 2.5 | 48.4 | 49.1 |
| Cloudy/Immiscible | 2.6 | 49.8 | 47.6 |
| Cloudy/Immiscible | 2.7 | 50.8 | 46.5 |
| Miscible | 4.7 | 89.6 | 5.7 |
| Miscible | 4.5 | 86.1 | 9.4 |
| Miscible | 4.2 | 78.9 | 16.9 |
| Miscible | 3.9 | 73.5 | 22.6 |
| Miscible | 3.6 | 67.7 | 28.8 |
| Miscible | 3.1 | 59.4 | 37.5 |
| Miscible | 2.9 | 55.6 | 41.5 |
| Cloudy/Immiscible | 2.8 | 52.7 | 44.6 |
| Miscible | 18.0 | 82.0 | 0.0 |
| Cloudy/Immiscible | 30.0 | 70.0 | 0.0 |
| Miscible | 25.0 | 75.0 | 0.0 |

This data shows that oxybenzone concentrations as high as 13% can be achieved in a water solution through the addition of ethyl-LGK as a cosolvent. Thus, higher concentrations of this UV agent can be tolerated in a formulation that contains water.

Example 3

Model Formulations with Salicylic Acid

Salicylic acid was pre-dissolved in ketal and then water was added at room temperature. Observations were made within 5 minutes. Results are shown in Table 5.

TABLE 5

| Result | wt. % Salicylic acid | wt. % Ethyl-LGK | wt. % water |
| --- | --- | --- | --- |
| Miscible | 15.0 | 85.0 | 0.0 |
| Miscible | 14.3 | 80.8 | 4.9 |
| Miscible | 13.6 | 76.9 | 9.5 |
| Miscible | 13.0 | 73.5 | 13.5 |
| Miscible | 12.4 | 70.4 | 17.2 |
| Miscible | 11.9 | 67.4 | 20.7 |
| Cloudy/Immiscible | 11.4 | 64.8 | 23.7 |
| Miscible | 11.8 | 66.6 | 21.6 |
| Miscible | 11.6 | 65.9 | 22.5 |
| Cloudy/Immiscible | 11.5 | 65.3 | 23.1 |
| Cloudy/Immiscible (literature) | 5.0 | 0.0 | 95.0 |
| Cloudy/Immiscible (literature) | 2.0 | 0.0 | 98.0 |
| Cloudy/Immiscible | 10.0 | 60.0 | 30.0 |
| Miscible | 5.0 | 60.0 | 35.0 |
| Cloudy/Immiscible | 5.0 | 54.9 | 40.1 |
| Miscible | 5.0 | 60.5 | 34.5 |
| Miscible | 5.0 | 67.4 | 27.7 |
| Miscible | 7.3 | 64.3 | 28.4 |
| Miscible | 5.0 | 68.0 | 27.0 |

This model formulation can be used alone as a serum, formulated with ethanol for an aqueous-alcohol base (a spray formulation, for instance), or used in an emulsion formulation.

Example 4

Ethanolic Aloe Vera Oil Solutions

Aloe vera oil is highly immiscible in both ethanol and isopropanol. Three-component mixtures of ethyl-LPK, aloe and either ethanol or isopropanol were prepared by mixing the materials at various proportions at room temperature in a vial and shaking. Results are shown in Table 6 (ethanol) and in Table 7 (isopropanol).

TABLE 6

| Result | % aloe vera oil | % ethanol | % Et-LPK |
| --- | --- | --- | --- |
| Cloudy/Immiscible | 5.0 | 95.0 | 0.0 |
| Miscible | 8.2 | 73.4 | 18.4 |

TABLE 6-continued

| Result | % aloe vera oil | % ethanol | % Et-LPK |
|---|---|---|---|
| Miscible | 12.0 | 67.9 | 20.1 |
| Miscible | 15.5 | 61.9 | 22.6 |
| Miscible | 20.3 | 59.4 | 20.3 |
| Miscible | 23.5 | 53.0 | 23.5 |
| Miscible | 26.8 | 46.4 | 26.8 |
| Miscible | 33.6 | 32.9 | 33.6 |
| Miscible | 35.0 | 30.1 | 35.0 |
| Miscible | 39.4 | 39.4 | 21.3 |
| Miscible | 42.6 | 14.8 | 42.6 |
| Miscible | 50.0 | 0.0 | 50.0 |
| Miscible | 70.0 | 20.0 | 10.0 |
| Miscible | 81.1 | 14.3 | 4.6 |
| Miscible | 90.0 | 5.0 | 5.0 |

TABLE 7

| Result | % aloe | % isopropanol | % Et-LPK |
|---|---|---|---|
| Cloudy/Immiscible | 30.0 | 70.0 | 0.0 |
| Miscible | 28.5 | 66.4 | 5.1 |
| Miscible | 37.0 | 55.5 | 7.6 |
| Miscible | 76.6 | 19.2 | 4.2 |
| Miscible | 87.5 | 9.7 | 2.7 |

These results show that the presence of ethyl-LPK allows very high concentrations of aloe vera oil to be dissolved into ethanolic or isopropanolic formulations. Those formulations are useful as sunscreens (with the addition of a UV additive) or as a soothing topical spray or lotion.

Example 5

Solubilization of Methyl Paraben

Three-component mixtures of Et-LGK, water, and methyl paraben were prepared by mixing the materials at various proportions at room temperature in a vial and shaking. Methyl paraben by itself is immiscible in water at the 1% by weight level. Results are shown in Table 8.

TABLE 8

| Result | % Methylparaben | % Ethyl LGK | % Water |
|---|---|---|---|
| Immiscible | 1.0 | 0.0 | 99.0 |
| Miscible | 3.6 | 37.1 | 59.3 |
| Miscible | 5.0 | 55.0 | 40.0 |
| Miscible | 10.2 | 57.6 | 32.2 |
| Miscible | 12.4 | 70.1 | 17.6 |
| Miscible | 13.0 | 73.5 | 13.5 |
| Miscible | 13.6 | 77.0 | 9.4 |
| Miscible | 14.3 | 80.9 | 4.9 |

The results show that Et-LGK/water cosolvent mixtures can dissolve up to 15% by weight methyl paraben.

Example 6

Solubilization of Propyl Paraben

Three-component mixtures of Et-LGK, water, and propyl paraben were prepared by mixing the materials at various proportions at room temperature in a vial and shaking. Propyl paraben by itself is immiscible in water at less than the 1% by weight level, and only to the 24% level in Et-LGK. Results are shown in Table 9.

TABLE 9

| Result | % Propylparaben | % Ethyl LGK | % Water |
|---|---|---|---|
| Cloudy/Immiscible | 5.0 | 0.0 | 95.0 |
| Miscible | 5.0 | 70.0 | 25.0 |
| Miscible | 10.0 | 70.0 | 20.0 |
| Miscible | 18.8 | 71.5 | 9.7 |
| Cloudy/Immiscible | 24.0 | 76.0 | 0 |

These results show that an Et-LGK/water cosolvent mixture can solubilize nearly 20% by weight of propyl paraben.

Example 7

Solubilization of Phenoxyethanol

Three-component mixtures of Et-LGK, water, and phenoxyethanol were prepared by mixing the materials at various proportions at room temperature in a vial and shaking. Phenoxyethanol by itself is immiscible in water at up to the 2% by weight level. Results are shown in Table 10.

TABLE 10

| Result | % Phenoxyethanol | % Ethyl LGK | % Water |
|---|---|---|---|
| Miscible | 2.0 | 0.0 | 98.0 |
| Immiscible | 5.0 | 0.0 | 95.0 |
| Miscible | 5.0 | 34.9 | 60.1 |
| Miscible | 10.1 | 50.0 | 39.9 |
| Miscible | 29.8 | 49.8 | 20.4 |
| Miscible | 41.2 | 41.2 | 17.6 |
| Miscible | 47.3 | 47.3 | 5.4 |

An Et-LGK/water cosolvent mixture can solubilize nearly 50% by weight of phenoxyethanol.

Example 8

Solubilization of Minoxidil

Solutions were prepared by combining ingredients from Table 11. All the ingredients were mixed into a vial, then heated to 75-80° C. until the minoxidil was dissolved. All mixtures were clear when hot. The mixtures were then removed from the heat source and allowed to cool to room temperature. Miscibility results are shown in Table 11.

TABLE 11

| Result | % Minoxidil | % ethanol | % DI water | % Ketal | Ketal |
|---|---|---|---|---|---|
| Miscible | 5 | 30 | 15 | 50 | Et-LGK |
| Miscible | 5 | 30 | 15 | 50 | Butyl-LGK |
| Miscible | 5 | 30 | 15 | 50 | LPK |
| Precipitated | 10 | 60 | 30 | 0 | None |

The results show that the formulation without the ketal precipitated within 1 hour, whereas the formulations with ketal remained clear.

Example 9

Solubilization of Polymers

This example shows the effect of alkyl ketal esters on solubility of various polymers. Results are shown in Table 12.

TABLE 12

| Polymer | % dissolved in Et-LGK | % dissolved in Et-LPK |
| --- | --- | --- |
| Nitrocellulose (from dried clear nail polish) | Y, minimally | Y |
| CAP-482-0.5 (cellulose acetate propionate) | 14 | ≥25 |
| CAB-381-0.5 (cellulose acetate butyrate) | 14 | ≥25 |
| Dermacryl 79 (acrylate/octylacrylamide copolymer) | ~5 | ~1 |
| PMMA | 1 | >10 |

These results show that all of the polymers tested dissolved to some extent in both Et-LGK and Et-LPK. The first three polymers are used in coatings (residential coatings, industrial coatings, or nail lacquer). The fourth polymer is an example of a waterproofing polymer used in sunscreen formulations.

Examples 10-41 show various personal care formulations and products that can be made using the alkyl ketal esters of structure I.

Example 10

Ethanolic Spray Sunscreen Solution

A model spray sunscreen formulation contained 64.4 parts ethanol, 3 parts of an acrylate/octylacrylamide copolymer, 3 parts of octyldodecanol, 7.5 parts of octinoxate, 4 parts of oxybenzone, 5 parts of octisalate, 3 parts of avobenzone, 2.5 parts of POLYCRYLENE® (CAS No. 862993-96-2), 2.5 parts of octocrylene and 5.1 parts of water.

Because ethanol is drying, it is desirable to reduce the ethanol concentration in the formulation. When 10 parts of the ethanol were replaced with 10 parts of either ethyl-LGK or ethyl-LPK, a stable solution was obtained that was less drying to the skin due to the reduction in ethanol content.

Example 11

Ethanolic Isopropyl Myristate Model Hand Sanitizer

Ethanol is a primary ingredient in many hand sanitizer formulations. The formulations typically contain one or more emollients such as isopropyl myristate. Water is also commonly added to these formulations to provide hydration or reduce cost, but this tends to make the solution cloudy due to the incompatibility of the emollient with water.

Thus, a formulation with 30 parts isopropyl myristate, 10 parts water, and 60 parts ethanol was cloudy. When the emollient level was dropped to 22% at the same water level, or when it was dropped to 27% with an increase in ethanol, a clear solution forms. In either case, the potential for dryness increases due to reduction in emollient or increase in ethanol. However, a clear solution containing 30% isopropyl myristate was obtained if 5 parts of water were replaced with 5 parts of ethyl-LGK; the complete formulation being 30 parts isopropyl myristate, 5 parts water, 5 parts ethyl-LGK and 60 parts ethanol. This formulation retained the balance of emollient and ethanol, while still providing hydration through the presence of water. Alternatively, a portion of the ethanol can be replaced with Et-LGK without sacrificing clarity, even at higher water levels. Thus, a clear solution was obtained when 27 parts isopropyl myristate was mixed with 9 parts of water, 9 parts of ethyl-LGK and 55 parts of ethanol. This reduced ethanol formulation was less drying.

Example 12

Sample Emulsion Lotion or Cream

A comparative lotion suitable for use as a moisturizing lotion was prepared in Example 12A. Examples 12B and 12C were prepared using 10 parts ethyl-LGK for an equivalent amount of the sesame seed oil and 10 parts ethyl-LPK for an equivalent amount of the sesame seed oil. A lotion can be from n-Butyl-LGK as shown in prospective Example 12D as shown in Table 13.

TABLE 13

| Ingredient (wt. %) | 12A | 12B | 12C | 12D |
| --- | --- | --- | --- | --- |
| Part A | | | | |
| Water (AQUA) | 70.46 | 70.5 | 70.45 | 70.48 |
| Disodium EDTA | 0.10 | 0.10 | 0.10 | 0.10 |
| Carbomer (Carbopol 980) | 0.26 | 0.25 | 0.25 | 0.25 |
| Methylpropanediol (MPdiol glycol) | 3.00 | 3.00 | 3.00 | 3.00 |
| 1,2-hexane diol | 1.00 | 0 | 0 | 0 |
| Part B | | | | |
| Steareth-2 (Brij 72) | 0.20 | 0.20 | 0.20 | 0.20 |
| PEG-100 stearate (Myrj 59 flaked) | 0.75 | 0.75 | 0.75 | 0.75 |
| Steareth-21 (Brij 721) | 1.00 | 1.00 | 1.00 | 1.00 |
| Cetearyl alcohol, ceteareth-20 (Lipowax D) | 1.50 | 1.50 | 1.50 | 1.50 |
| Et-LGK | 0 | 10.00 | 0 | 0 |
| Et-LPK | 0 | 0 | 10.00 | 0 |
| n-BuLGK | 0 | 0 | 0 | 10 |
| *Sesamum indicum* (sesame) seed oil | 20.00 | 10.0 | 10.00 | 10p |
| Part C | | | | |
| Triethanolamine | 0.24 | 0.2 | 0.25 | 0.22 |
| Part D | | | | |
| Hydroxyethyl acrylate/sodium acryloyldimethyl taurate copolymer squalane polysorbate 60 (Simulgel NS) | 1.50 | 1.50 | 1.5 | 1.5 |

To prepare the moisturizing lotions, Part A was first prepared by dissolving the disodium EDTA into the water. Carbopol was slowly added and mixed until fully hydrated. The remaining Part A ingredients were added and Part A was heated to 75° C. The ingredients of Part B were combined under mixing at 75° C. Once uniform, Part B was slowly added to Part A with moderate agitation. Once uniform, the solution was cooled to 60-65° C. Part C was then used to adjust the pH to 5.5-6.0 and the batch was cooled to 40° C. Part D was then added to the batch with mixing and then homogenized for 5 minutes or until uniform at 3500 rpm. Further amounts of Part D were added if necessary to adjust the viscosity to 15,000-25,000 cps.

In Examples 12B and 12C, the result was a light, less greasy formulation compared to comparative example 12A. Lotions 12B and 12C also had a silky after-feel absent from example 12A. All formulations remained kinematically stable. Example 12B further had the further advantage of being an effective makeup remover. It is expected that Example 12D will also be a light, less greasy kinematically stable product.

Example 13

PMMA Serum Base

Polymethyl methacrylate (PMMA) is used to achieve a soft-focus effect that hides the appearance of wrinkles. Normally, PMMA is delivered in an emulsion formulation such as a cream or lotion, or as a powder, as it is not soluble in either water or ethanol. However, PMMA was soluble in ethyl-LPK to the extent of 5 parts of PMMA in 95 parts of ethyl-LPK, and nearly to the same extent in mixtures of ethyl-LPK and ethyl-LGK. PMMA was also soluble in various cosolvent mixtures of ethanol and ethyl-LPK or ethanol, water and ethyl-LPK. Therefore, the following in Table 13 are examples of clear serum bases that contained dissolved PMMA, and which formed by themselves, or in admixture with other materials, solution forms that contained dissolved PMMA.

TABLE 14

| Serum Base | PMMA | Ethyl-LPK | ethanol | water |
|---|---|---|---|---|
| | | wt. % | | |
| A | 3.1 | 58.1 | 38.9 | 0 |
| B | 3 | 56.5 | 38.7 | 1.8 |
| C | 2.5 | 47.7 | 32.6 | 17.7 |
| D | 4.6 | 88 | 7.4 | 0 |

Examples 14-15

Sunscreen Lotion

Model sunscreen lotions were made from the ingredients shown in Table 14.

TABLE 14

| Ingredients | Ex. 14 wt. % | Ex. 15 wt. % |
|---|---|---|
| Et-LPK | 0 | 1 |
| Cetyl alcohol | 1 | 0 |
| Stearic acid | 2 | 2 |
| Octyl palmitate | 3 | 3 |
| Octylmethoxyl cinnamate | 7.5 | 7.5 |
| Oxybenzone | 3 | 3 |
| PEG-40 stearate | 1.5 | 1.5 |
| Dimethyl stearamine | 2 | 2 |
| Acrylates/octylacrylamide copolymer (Dermacryl 79) | 2 | 2 |
| Deionized water | To 100 | To 100 |
| Crosslinked polyacrylate copolymer (Carbopol ETD 2050)* | 0.06 | 0.06 |
| Triethanolamine | 0.7 | 0.7 |

*The amount of thickener should be adjusted based on the efficiency of the carbopol grade To prepare the sunscreen lotion formulations, Part B was first prepared by adding the carbomer slowly into the water with mixing and heated to 80° C. The triethanol amine was then added to complete Part B. In a separate vessel, the ingredients from Part A were combined except for the acrylates/octylacrylamide copolymer. These components were heated to 80° C. with mixing. The acrylates/octylacrylamide copolymer was then slowly sifted into Part A under constant stirring until dissolved. Part A was then added to Part B and mixed for 15 minutes at 80° C. The mixture was then slowly cooled to room temperature. Example 15 was less viscous, but remained stable for at least four weeks. The modified product had a lighter, less greasy feel.

Example 16

Surfactant-Free Cosmetics Remover

Comparative cosmetic remover A and inventive cosmetic removers 13-A through 13-D were prepared from the following formulations. The formulations were clear in all cases except for comparative A, which was hazy. The formulations were evaluated by rubbing them onto a mascara-coated acrylonitrile-butadiene-styrene sheets, using a cotton swab. A "G" rating indicates that the mascara was removed from the substrate after several rubs; a "VG" rating indicates that the mascara was removed from the substrate with minimal rubbing. Results are shown in Table 15.

TABLE 15

| | Parts by Weight | | | | |
|---|---|---|---|---|---|
| Component | A* | 17-A | 17-B | 17-C | 17-D |
| Sulfosuccinate salt | 5.0 | 0 | 0 | 0 | 0 |
| 1,2-Propylene glycol | 45.3 | 70.0 | 0 | 0 | 0 |
| Glycerin | 47.0 | 0 | 0 | 0 | 0 |
| PEG-7 glyceryl cocoate | 2 | 0 | 0 | 0 | 0 |
| Paraben DU | 0 | 1 Drop | 1 Drop | 1 Drop | 1 Drop |
| Ethyl-LPK | 0 | 30.0 | 44.4 | 30.0 | 25.0 |
| Ethyl-LGK | 0 | 0 | 27.8 | 30.0 | 25.0 |
| 1,3-propane diol | 0 | 0 | 27.8 | 40.0 | 50.0 |
| Water | 0 | 0 | 0 | 0 | 0 |
| Rating | G | VG | VG | VG | VG |

*Not an example of the invention

As can be seen from the foregoing table, the presence of a sparingly water-soluble alkyl ketal ester provides the benefits of high effectiveness, the elimination of surfactant and higher formulation stability, as indicated by the better compatibility of the inventive mixtures. In addition, an all-naturally-derived formulation (apart from the paraben preservatives) was provided in examples 13-B, 13-C, and 13-D.

Example 17

Model Insecticide Formulations

Three-component mixtures of N,N-diethyl-m-toluamide (DEET), ethyl-LGK, and water were prepared by mixing the materials at various proportions at room temperature in a vial and shaking. A clear mixture was obtained when 26.7 parts of DEET were mixed with 60.5 parts of ethyl-LGK and 12.8 parts of water. This mixture was effective as a water-based insecticide.

Because DEET is soluble in ethanol and ethyl-LPK, an ethanolic insecticide can be prepared that comprises DEET dissolved in a cosolvent mixture of ethanol and ethyl-LPK. The presence of the ethyl-LPK allows the ethanol concentration to be reduced, to produce a less drying insecticide formulation.

Examples 18-24

Lipstick Containing Water

A lipstick (Example 18) was prepared from the ingredients in Table 16.

TABLE 16

| | Ingredient | wt. % |
|---|---|---|
| Part A | Caprylic/Capric triglyceride | 8.56 |
| | Octyldodecyl stearoyl stearate | 13.37 |
| | Triisostearyl citrate | 4.05 |
| | Pentaerythrityl tetraisostearate | 5.60 |
| | Jojoba esters | 1.72 |
| | Lanolin oil | 1.62 |
| | Bis-diglyceryl polyacyladipate-2 | 1.02 |
| | *Ricinus communis* (Castor) Seed Oil | 30.50 |
| | *Copernicia cerifera* (Carnauba) Wax | 2.30 |
| | *Euphorbia cerifera* (Candelilla) Wax | 5.24 |
| | Cera Alba (Beeswax) | 2.09 |
| | Ozokerite Wax | 1.80 |
| | Microcrystalline Wax | 1.13 |
| | Phenoxyethanol | 1.00 |
| | Polyethylene | 1.00 |
| | Octyl Methoxycinnamate | 0.60 |
| | Tocopheryl Acetate | 0.05 |
| Part B | *Ricinus Communis* (Castor) Seed Oil | 10.00 |
| | D&C Red No. 6 Barium Lake | 6.25 |
| | Iron Oxide | 0.10 |
| Part C | 50% mixture of Et-LGK and Purified Water | 2.00 |

To prepare the lipstick, the Part A ingredients were heated to 80-85 C with mixing. The ingredients of Part B were pre-ground. When the Part A wax/oil mixture was completely melted and clear, the Part B color grind was added to Part A wax/oil mixture. When all the color was dispersed and the batch was uniform, the batch was dropped to a temperature of 75° C. and the Part C solution was slowly added to the batch and mixed until the batch was completely homogeneous. When the batch was uniform, the formulation was poured into molds to cool.

Lipsticks (Examples 19-24) were prepared from the ingredients in Table 17.

TABLE 17

| Ingredient | 19 wt. % | 20 wt. % | 21 wt. % | 22 wt. % | 23 wt. % | 24 wt. % |
|---|---|---|---|---|---|---|
| Part A | | | | | | |
| Caprylic/Capric Triglyceride | 8.56 | 8.56 | 8.56 | 8.56 | 8.56 | 8.56 |
| Octyldodecyl Stearoyl Stearate | 13.37 | 13.37 | 13.37 | 13.37 | 13.37 | 13.37 |
| Triisostearyl Citrate | 4.05 | 4.05 | 4.05 | 4.05 | 4.05 | 4.05 |
| Pentaerythrityl Tetraisostearate | 5.60 | 5.60 | 5.60 | 5.60 | 5.60 | 5.60 |
| Jojoba Esters | 1.72 | 1.72 | 1.72 | 1.72 | 1.72 | 1.72 |
| Lanolin Oil | 1.62 | 1.62 | 1.62 | 1.62 | 1.62 | 1.62 |
| Bis-Diglyceryl Polyacyladipate-2 | 1.02 | 1.02 | 1.02 | 1.02 | 1.02 | 1.02 |
| *Copernicia Cerifera* (Carnauba) Wax | 2.30 | 2.30 | 2.30 | 2.30 | 2.30 | 2.30 |
| *Euphorbia Cerifera* (Candelilla) Wax | 5.24 | 5.24 | 5.24 | 5.24 | 5.24 | 5.24 |
| *Ricinus Communis* (Castor) Seed Oil | 10.50 | 10.50 | 10.50 | 10.50 | 10.50 | 10.50 |
| Cera Alba (Beeswax) | 2.09 | 2.09 | 2.09 | 2.09 | 2.09 | 2.09 |
| Ozokerite Wax | 1.80 | 1.80 | 1.80 | 1.80 | 1.80 | 1.80 |
| Microcrystalline Wax | 1.13 | 1.13 | 1.13 | 1.13 | 1.13 | 1.13 |
| Phenoxyethanol | 1.00 | 1.00 | 1.00 | 1.00 | 1.00 | 1.00 |
| Polyethylene | 1.00 | 1.00 | 1.00 | 1.00 | 1.00 | 1.00 |
| Octyl Methoxycinnamate | 0.60 | 0.60 | 0.60 | 0.60 | 0.60 | 0.60 |
| Tocopheryl Acetate | 0.05 | 0.05 | 0.05 | 0.05 | 0.05 | 0.05 |
| Part B | | | | | | |
| *Ricinus Communis* (Castor) Seed Oil | 18.00 | 16.00 | 14.00 | 12.00 | 10.00 | 2.00 |
| Part C | | | | | | |
| *Ricinus Communis* (Castor) Seed Oil | 10.00 | 10.00 | 10.00 | 10.00 | 10.00 | 10.00 |
| D&C Red No. 6 Barium Lake | 6.25 | 6.25 | 6.25 | 6.25 | 6.25 | 6.25 |
| Iron Oxide | 0.10 | 0.10 | 0.10 | 0.10 | 0.10 | 0.10 |
| Part D | | | | | | |
| 50% mixture of Et-LGK and Purified Water | 4.00 | 6.00 | 8.00 | 10.00 | 12.00 | 20.00 |

To prepare the lipsticks, Part A was heated at 80-85° C. with mixing. When Part A was completely melted and clear, Part B was added to Part A while mixing. Part C was pre-ground. When Part A/B was completely melted and clear, Part C color grind was added to the combined Parts A and B. When all the color was dispersed and the batch was uniform, the batch temperature was dropped to 75 C and the Part D solution was slowly added to the batch with mixing. The batch was mixed until completely homogeneous. When the batch was uniform, it was poured into molds to cool.

Alternatively, Part D can be added to combined Parts A and B before addition of Part C, though care should be taken to avoid or minimize water loss.

The lipstick structure was good in each of Examples 15-21. Samples were aged at 45° C. for 4 weeks to determine stability, and it was found that none of the sticks sweated, showed signs of condensation, or softened when returned to room temperature. There were further no signs of color bleed or color change.

Water content was verified for Examples 20-25 as follows. Lipsticks were dried in a vacuum oven at 35° C. for 24 hours and the weight loss was monitored. The observed mass loss was consistent with the weight loss expected from evaporation of the charged mass of water in the lipstick. Results are shown in Table 18.

TABLE 18

| Lipstick Example | Charged water (wt. %) | Mass Loss (wt. %) | % of expected |
|---|---|---|---|
| 19 | 2 | 1.16 | 57.9 |
| 20 | 3 | 3.1 | 103 |
| 21 | 4 | 3.4 | 84.9 |
| 22 | 5 | 4.9 | 97.9 |
| 23 | 6 | 6.6 | 110 |
| 24 | 10 | 10.6 | 106 |

Examples 26 and 27

Hair Dye Formulations

Hair dye formulations were prepared from the ingredients in Table 19.

TABLE 19

| Ingredient (wt. %) | 26A | 27A | 26B | 27B |
| --- | --- | --- | --- | --- |
| Water | 60.19 | 60.19 | 60.19 | 60.19 |
| Alkyl polyglucoside | 1.76 | 1.76 | 1.76 | 1.76 |
| Oleic acid | 14.00 | 14.00 | 14.00 | 14.00 |
| Nonoxynol-1 | 3.70 | 3.70 | 3.70 | 3.70 |
| Nonoxynol-4 | 5.00 | 5.00 | 5.00 | 5.00 |
| EDTA (4Na) | 0.05 | 0.05 | 0.05 | 0.05 |
| Et-LGK | 7.00 | 7.00 | 0 | 0 |
| Et-LPK | 0 | 0 | 7.00 | 7.00 |
| Isopropanol 99% | 7.00 | 7.00 | 7.00 | 7.00 |
| Ammonium hydroxide | 0.80 | 0.80 | 2.10 | 2.10 |
| Erythorbic acid | 0.40 | 0.40 | 0.40 | 0.40 |
| Sodium sulfite | 0.10 | 0.10 | 0.10 | 0.10 |
| qs. to pH |  |  |  |  |
| Final pH | 10.2 | 8.5 | 10.2 | 8.5 |

Saturated solutions of each oxidation dye intermediate were prepared in Examples 26A and 27A at pH 10.2, and Examples 26B and 27B at pH 8.5. Three replications were prepared for each example. The saturated solutions were prepared by equilibrating three 50 g samples of each of the variations at 27° C. in a water bath. Once the bases were at the desired temperature, excessive amounts (i.e., more than would dissolve) of p-phenylenediamine, 1-naphthol and p-toluenedaimine sulfate were added to portions of each base pH combinations. The resultant mixtures were maintained at 27° C. for 10 minutes with stirring to dissolve the maximum possible amount of each intermediate under these conditions.

At the end of the 10 minutes the samples were withdrawn from the water bath and pipetted to 500 ppm in Solvent A then scanned in a UV-Vis spectrophotometer and compared to a calibration curve of known dye concentration in a standard solvent (Solvent A, below) to determine concentration.

A calibration curve for dye concentration was prepared by preparing 1.0% (w/w) solutions of the oxidation dye intermediates: p-phenylenediamine (PPD), 1-naphthol and p-toluenediamine sulfate (PTD) were prepared in Solvent A (0.2% EDTA, 0.4% erythorbic acid, 0.4% sodium sulfite, 49.5% DI water (RO filtered), and 49.5% isopropanol). The solutions were diluted stepwise from 1.00% to 0.00001% (10 ppm) and scanned with a Varian DSM 200 from a range of 380 nm to 900. Absorption maxima in the visible range were used to plot concentration curves with an optimal absorbance for viewing at approximately 500 ppm. Results are shown in Table 20.

TABLE 20

|  | Ingredient | 26A | 26B | 27A | 27B |
| --- | --- | --- | --- | --- | --- |
| Average Solubility % wt./wt. | p-phenylenediamine | 0.07 | 0.07 | 0 | <0.01 |
|  | 1-naphthol | 0.14 | 0.08 | 0.01 | <0.01 |
|  | p-toluenediamine sulfate | 0.35 | 0 | 0.01 | 0 |
| Visual |  | Clear | Clear | Trapped bubbles | Clear |

All formulations resulted in viscosities of less than 150 cP on a Brookfield RVT, except for 34B, which formed a gel with a viscosity of greater than 5000 cP. All formulations were initially clear, except formulation 26A, which had trapped bubbles that produced a cloudy, yet translucent, formulation.

Examples 28 and 29

Self-Tanning Model Formulations

Self-tanning model formulations, one water-based (Example 39) and one alcohol-based (Example 40) were prepared from the ingredients in Table 21.

TABLE 21

| Ingredient (g) | 28 - Water Based | 29 - Alcohol Based |
| --- | --- | --- |
| DI water | 3 | 0 |
| Ethanol | 0 | 5 |
| Dihydroxyacetone | 1 | 0.5 |
| Erythrulose | 0.5 | 0.25 |
| Et-LGK | 4 | 0 |
| Et-LPK | 0 | 5 |

Dihydroxyacetone was purchased from makingcosmetics.com. The recommended dosage level depends on the desired degree of tanning. Concentrations of 2-12% in the final formulation are typical. The preferred pH of a formulation with dihydroxyacetone and ketal is 5.5.

Example 30

Anti-Acne Active Agents

Salicylic Acid

Salicylic acid (U.S.P. grade is available from J. T. Baker) was dissolved at 15% solids and 20.8% solids in Et-LGK at room temperature and 50° C., respectively. Both mixtures formed clear uniform solutions at room temperature initially. The mixture at 15% solids was still soluble after 24 hours of storage at room temperature, whereas the mixture at 20.8% solids precipitated.

Salicylic acid was dissolved at 10% solids in Bu-LGK at 80° C. After 24 hours at room temperature, there was no evidence of precipitation.

Salicylic acid was dissolved at 11% solids in Et-LPK with no heat. After 24 hours at room temperature, there was no evidence of precipitation. A mixture at 14.3% solids dissolved when heated but precipitated out at room temperature.

Benzoyl Peroxide

Benzoyl peroxide (USP grade, available as Luperox A70S from Arkema) was dissolved at 5% solids in Et-LGK at 35° C. The solution showed no signs of precipitation after 24 hours at room temperature. A solution at 9.5% solids precipitated at room temperature.

Retinoic Acid (all Trans)

Retinoic acid (Tretinoin, available from Tokyo Chemical Industry) was dissolved at 2.2% solids in Et-LGK at 80° C. After 1 day at room temperature, there was no sign of precipitation.

Retinoic acid was dissolved in Bu-LGK at room temperature at 0.25%. After 1 day at room temperature, there was no sign of precipitation. A mixture at 0.5% retinoic acid formed a dispersion.

Retinoic acid was dissolved in Et-LPK at 0.5% solids at room temperature. After 1 day at room temperature, there was no sign of precipitation. Retinoic acid was dissolved in Et-LPK at 0.84% solids at room temperature. After 1 day at room temperature, there was no sign of precipitation. Retinoic acid was insoluble in Et-LPK at 1.88% solids at room temperature. Retinoic acid was soluble in Et-LPK at 1.88% solids at 80° C.

Tea Tree Oil

Certified organic tea tree oil (*Melaleuca alternifolia*, plant sourced from Australia and extracted by steam distillation) was purchased from Wyndmere Naturals.

A 50/50 mixture of Et-LGK and tea tree oil was miscible at room temperature.

A 50/50 mixture of Bu-LGK and tea tree oil was miscible at room temperature.

A 50/50 mixture of Et-LPK and tea tree oil was miscible at room temperature.

Example 31

Anti-Aging Active Agents

Salicylic Acid

Salicylic acid (U.S.P. grade available from J. T. Baker) was dissolved at 15% solids and 20.8% solids in Et-LGK at room temperature and 50° C., respectively. Both mixtures formed clear uniform solutions at room temperature initially. The mixture at 15% solids was still soluble after 24 hours of storage at room temperature, whereas the mixture at 20.8% solids precipitated.

Salicylic acid was dissolved at 10% solids in Bu-LGK at 80° C. After 24 hours at room temperature, there was no evidence of precipitation.

Salicylic acid was dissolved at 11% solids in Et-LPK with no heat. After 24 hours at room temperature, there was no evidence of precipitation. A mixture at 14.3% solids dissolved when heated but precipitated out at room temperature.

Lactic Acid

Lactic acid (available from Alfa Chem, Ashland Distribution, and Spectrum Chemical Mfg. Corp) forms a homogeneous solution in Et-LGK at a 50/50 ratio. Lactic acid formed a homogeneous solution in Et-LPK at a 50/50 ratio.

Glycolic Acid

Glycolic acid (available from Lipo Chemicals, Inc. and Spectrum Chemical Mfg. Corp.) was dissolved at 8.33% solids in Et-LGK at room temperature and formed a homogeneous solution. Glycolic acid at 10% solids in Et-LGK did not form a homogeneous solution at room temperature.

Glycolic acid at 4.35% solids in Et-LPK did not form a homogeneous solution at room temperature.

Ubiquinone (Coenzyme Q10)

A solution of 3.7% Coenzyme Q10 in Et-LGK was insoluble at room temperature.

A solution of 5% Coenzyme Q10 in Bu-LGK was insoluble at room temperature.

A solution of 3.3% Coenzyme Q10 in Et-LPK was soluble at room temperature.

A solution of 20% Coenzyme Q10 in Et-LPK was soluble at room temperature.

Dimethylmethoxy Chromanyl Palmitate

Dimethylmethoxy chromanyl palmitate (available as Chromabright from Liopotec) at 2.03% formed a homogeneous solution in Et-LGK with heat.

Dimethylmethoxy chromanyl palmitate at 2% formed a homogeneous solution in Et-LPK at room temperature.

The recommended dosage level is 0.1%.

Tetrahydrodiferuloylmethane (Tetrahydrodiferuloylmethane)

Tetrahydrocurcuminoids (available from lotioncrafter.com) was dissolved at 20% solids in Et-LGK at room temperature to form a clear uniform solution. The mixture was still soluble after 24 hours of storage at room temperature.

Tetrahydrocurcuminoids was dissolved at 5% solids in Bu-LGK at 50° C. to form a clear uniform solution. The mixture was still soluble after 24 hours of storage at room temperature.

Tetrahydrocurcuminoids was dissolved at 5% solids in Et-LPK at 50° C. to form a clear uniform solution. The mixture was still soluble after 24 hours of storage at room temperature.

The recommended usage rate is 0.1-1%.

Resveratrol

Resveratrol (available from Enzo Life Sciences) was dissolved at 1% solids in Et-LGK at room temperature. The mixture was still soluble after 24 hours of storage at room temperature.

Resveratrol was dissolved at 0.5% solids in Bu-LGK at 50° C. The mixture was still soluble after 24 hours of storage at room temperature.

Resveratrol was dissolved at 0.5% solids in Et-LPK at 50° C. The mixture was still soluble after 24 hours of storage at room temperature.

Tetrahydropiperine

Tetrahydropiperine (available as Cosmoperine from lotioncrafter.com) was dissolved at 20% solids in Et-LGK at room temperature. The mixture was still soluble after 24 hours of storage at room temperature.

Tetrahydropiperine was dissolved at 20% solids in Bu-LGK at room temperature. The mixture was still soluble after 24 hours of storage at room temperature.

Tetrahydropiperine was dissolved at 20% solids in Et-LPK at room temperature. The mixture was still soluble after 24 hours of storage at room temperature. Tetrahydropiperine is a co-ingredient in anti-aging formulations and is thought to improve the bioavailability of active agents.

Dimethylmethoxy Chromanol

Dimethylmethoxy Chromanol (available as Lipochroman-6 from lotioncrafter.com) was dissolved at 2.5% solids in Et-LGK at room temperature. The mixture was still soluble after 24 hours of storage at room temperature.

Dimethylmethoxy Chromanol was dissolved at 2.5% solids in Bu-LGK at room temperature. The mixture was still soluble after 24 hours of storage at room temperature.

Dimethylmethoxy Chromanol was dissolved at 2.5% solids in Et-LPK at room temperature. The mixture was still soluble after 24 hours of storage at room temperature.

The recommended usage rate is 0.01-0.05%.

Example 32

Anti-Fungal/Anti-Bacterial/Anti-Microbial Agents

Tea Tree Oil

A 50/50 mixture of Et-LGK and tea tree oil was miscible at room temperature.

A 50/50 mixture of Bu-LGK and tea tree oil was miscible at room temperature.

A 50/50 mixture of Et-LPK and tea tree oil was miscible at room temperature.

Parabens

Methyl paraben (available from EMD Chemicals, Jeen International Corporation, and The Hallstar Company) was dissolved at 15% solids and 20.8% solids in Et-LGK at room temperature and 50° C., respectively. Both mixtures formed clear uniform solutions at room temperature initially. The mixture at 15% solids was still soluble after 24 hours of storage at room temperature, whereas the mixture at 20.8% solids precipitated.

Propyl paraben was dissolved at 15% solids and 20.8% solids in Et-LGK at room temperature and 50° C., respectively. Both mixtures formed clear uniform solutions at room temperature initially and remained as clear uniform solutions after 24 hours of storage at room temperature.

Caprylyl Glycol

Caprylyl glycol (available from Inolex as Lexgard O) was dissolved at 15% solids and 20.8% solids in Et-LGK at room temperature. Both mixtures formed clear uniform solutions at room temperature initially and remained as clear uniform solutions after 24 hours of storage at room temperature.

Phenoxyethanol

Phenoxyethanol (available from Dow Chemical and Spectrum Chemical) was soluble at 15% and 20.8% in Et-LGK at room temperature. Both mixtures formed clear uniform solutions at room temperature initially and remained as clear uniform solutions after 24 hours of storage at room temperature.

Example 33

Dandruff Active Agents

Salicylic Acid

Salicylic acid (U.S.P. grade available from J. T. Baker) was dissolved at 15% solids and 20.8% solids in Et-LGK at room temperature and 50° C., respectively. Both mixtures formed clear uniform solutions at room temperature initially. The mixture at 15% solids was still soluble after 24 hours of storage at room temperature, whereas the mixture at 20.8% solids precipitated.

Salicylic acid was dissolved at 10% solids in Bu-LGK at 80° C. After 24 hours at room temperature, there was no evidence of precipitation.

Salicylic acid was dissolved at 11% solids in Et-LPK with no heat. After 24 hours at room temperature, there was no evidence of precipitation. A mixture at 14.3% solids dissolved when heated but precipitated out at room temperature.

Tea Tree Oil

A 50/50 mixture of Et-LGK and tea tree oil was miscible at room temperature.

A 50/50 mixture of Bu-LGK and tea tree oil was miscible at room temperature.

A 50/50 mixture of Et-LPK and tea tree oil was miscible at room temperature.

Resveratrol

Resveratrol (available from Enzo Life Sciences) was dissolved at 1% solids in Et-LGK at room temperature. The mixture was still soluble after 24 hours of storage at room temperature.

Resveratrol was dissolved at 0.5% solids in Bu-LGK at 50° C. The mixture was still soluble after 24 hours of storage at room temperature.

Resveratrol was dissolved at 0.5% solids in Et-LPK at 50° C. The mixture was still soluble after 24 hours of storage at room temperature.

Example 34

Hair Dyes p-Phenylene Diamine p-Phenylene diamine (97% purity, available from Alfa Aesar) was dissolved at 5% solids in Et-LGK at 80° C. and formed a very dark solution with no evidence of precipitation. The active was still soluble after 24 hours of storage at room temperature.

p-Phenylene diamine partially dissolved at 25% solids in Bu-LGK at 80° C. and formed a dark solution with precipitant on the bottom. p-phenylene diamine was dissolved at 5% solids in Bu-LGK at 80° C. and formed a very dark solution with no evidence of precipitation.

p-Phenylene diamine did not completely dissolve at 5% solids in Et-LPK 80° C. An orange solution with precipitant formed. p-phenylene diamine did not completely dissolve at 1% solids in Et-LPK 80° C. An orange solution with precipitant formed. In both cases, the solution turned darker orange with time during storage at room temperature but precipitant remained.

p-Toluenediamine Sulfate p-Toluenediamine sulfate (97% purity, available from Aldrich) partially dissolved at 1% solids in Et-LGK at 80° C. The sample formed a brown solution with solid precipitant on the bottom. p-Toluenediamine sulfate partially dissolved at 0.1% solids in Et-LGK at 80° C. The sample formed a brown solution with solid precipitant on the bottom.

p-Toluenediamine sulfate failed to dissolve at both 1% solids and 0.1% solids in Et-LPK at 80° C. The sample formed milky white mixture with solids at the bottom of the vial. No color development occurred.

Resorcinol

Resorcinol (at 99% purity available from Alfa Aesar) was dissolved at 10% solids in Et-LGK at 80° C. with agitation. The mixture was still soluble after 24 hours of storage at room temperature.

Resorcinol was dissolved at 10% solids in Bu-LGK at 80° C. with agitation. The mixture was still soluble after 24 hours of storage at room temperature.

Resorcinol was dissolved at 10% solids in Et-LPK at room temperature with agitation. The mixture was still soluble after 24 hours of storage at room temperature.

m-Aminophenol m-Aminophenol was dissolved at 5% solids in Et-LGK at room temperature. The mixture was still soluble after 24 hours of storage at room temperature.

m-Aminophenol was dissolved at 5% solids in Et-LPK at 80° C. with agitation. The mixture was still soluble after 24 hours of storage at room temperature.

Example 35

Insect Repellant

N,N-Diethyl-m-toluamide (DEET)

A 50/50 mixture of Et-LGK and DEET (98.25% purity available as OFF! Deep Woods Sportsmen) was miscible at room temperature.

A 50/50 mixture of Et-LPK and DEET was miscible at room temperature.

Citronella

A 50/50 mixture of Et-LGK and citronella pure essential oil (*Cymbopogon nardus*, plant sourced from Indonesia and extracted by steam distillation) was purchased from Wyndmere Naturals) was miscible at room temperature.

A 50/50 mixture of Bu-LGK and citronella pure essential oil was miscible at room temperature.

A 50/50 mixture of Et-LPK and citronella pure essential oil was miscible at room temperature.

Example 36

Example Medicinal Active Agents

Retinoic Acid (all Trans)

Retinoic acid (Tretinoin, available from Tokyo Chemical Industry) was dissolved at 2.2% solids in Et-LGK at 80° C. After 1 day at room temperature, there was no sign of precipitation.

Retinoic acid was dissolved in Bu-LGK at room temperature at 0.25%. After 1 day at room temperature, there was no sign of precipitation. A mixture at 0.5% retinoic acid formed a dispersion.

Retinoic acid was dissolved in Et-LPK at 0.5% solids at room temperature. After 1 day at room temperature, there was no sign of precipitation. Retinoic acid was dissolved in Et-LPK at 0.84% solids at room temperature. After 1 day at room temperature, there was no sign of precipitation. Retinoic acid was insoluble in Et-LPK at 1.88% solids at room temperature. Retinoic acid was soluble in Et-LPK at 1.88% solids at 80° C.

Salicylic Acid

Salicylic acid was dissolved at 15% solids and 20.8% solids in Et-LGK at room temperature and 50° C., respectively. Both mixtures formed clear uniform solutions at room temperature initially. The mixture at 15% solids was still soluble after 24 hours of storage at room temperature, whereas the mixture at 20.8% solids precipitated.

Salicylic acid was dissolved at 10% solids in Bu-LGK at 80° C. After 24 hours at room temperature, there was no evidence of precipitation.

Salicylic acid was dissolved at 11% solids in Et-LPK with no heat. After 24 hours at room temperature, there was no evidence of precipitation. A mixture at 14.3% solids dissolved when heated but precipitated out at room temperature.

Tea Tree Oil

A 50/50 mixture of Et-LGK and tea tree oil was miscible at room temperature.

A 50/50 mixture of Bu-LGK and tea tree oil was miscible at room temperature.

A 50/50 mixture of Et-LPK and tea tree oil was miscible at room temperature.

Resveratrol

Resveratrol was dissolved at 1% solids in Et-LGK at room temperature. The mixture was still soluble after 24 hours of storage at room temperature.

Resveratrol was dissolved at 0.5% solids in Bu-LGK at 50° C. The mixture was still soluble after 24 hours of storage at room temperature.

Resveratrol was dissolved at 0.5% solids in Et-LPK at 50° C. The mixture was still soluble after 24 hours of storage at room temperature.

Example 37

Skin Whitening

Tetrahydrodiferuloylmethane

Tetrahydrocurcuminoids (tetrahydrodiferuloylmethane, available as Tetrahydrocurcuminoids (THC) from lotioncrafter.com) was dissolved at 20% solids in Et-LGK at room temperature to form a clear uniform solution. The mixture was still soluble after 24 hours of storage at room temperature.

Tetrahydrocurcuminoids was dissolved at 5% solids in Bu-LGK at 50° C. to form a clear uniform solution. The mixture was still soluble after 24 hours of storage at room temperature.

Tetrahydrocurcuminoids was dissolved at 5% solids in Et-LPK at 50° C. to form a clear uniform solution. The mixture was still soluble after 24 hours of storage at room temperature.

The recommended usage rate is 0.1-1%.

Hydroquinone

Hydroquinone (available in 99% purity from Alfa Aesar) was dissolved at 5% solids in Et-LGK at 80° C. with agitation to form a clear uniform solution. The mixture was still soluble after 24 hours of storage at room temperature.

Hydroquinone was dissolved at 10% solids in Et-LPK at 80° C. with agitation to form a clear uniform solution. The mixture was still soluble after 24 hours of storage at room temperature.

Dimethylmethoxy Chromanyl Palmitate

Dimethylmethoxy chromanyl palmitate (available as Chromabright from Liopotec) at 2.03% formed a homogeneous solution in Et-LGK with heat.

Dimethylmethoxy chromanyl palmitate at 2% formed a homogeneous solution in Et-LPK at room temperature.

The recommended dosage level of dimethylmethoxy chromanyl palmitate is 0.1% by weight.

Example 38

Tanning Active Agents

Eryhthrulose

Erythrulose and Et-LGK were mixed at a ratio of 10/90 at room temperature and formed a clear uniform solution. The mixture was still soluble after 24 hours of storage at room temperature.

Erythrulose and Bu-LGK were mixed at a ratio of 10/90 at room temperature; the two liquids separated into distinct phases.

Erythrulose and Et-LPK were mixed at a ratio of 10/90 at room temperature; the two liquids separated into distinct phases.

Concentrations of 2-8% in the final formulation are typical. Erythrulose is commonly formulated with dihydroxyacetone.

Example 39

UV Active Agents

Avobenzone (Butyl Methoxydibenzoylmethane)

Avobenzone (available from Symrise as Neo Heliopan 357 and as Escalol 517 by International Specialty Formulations, Inc. (ISP)) was dissolved at 25% solids in Et-LGK with heat and formed a clear, uniform solution. After 24 hours at room temperature, a precipitate formed. Avobenzone was dissolved at 20% solids in Et-LGK with heat and formed a clear, uniform solution. After 5 days at room temperature, there was no evidence of precipitation.

Avobenzone was dissolved at 10% solids in Bu-LGK at 80° C. After 24 hours at room temperature, there was no evidence of precipitation.

Avobenzone was dissolved at 35% solids in Et-LPK with heat and formed a clear, uniform solution. After 24 hours at room temperature, a precipitate formed. Avobenzone was dissolved at 30% solids in Et-LPK with heat and formed a clear, uniform solution. After 24 hours at room temperature, there was no evidence of precipitation. The solution showed no signs of precipitation after 5 days.

Oxybenzone (Benzone-3)

Oxybenzone (available from BASF as UVINUL M40, Acros Organics (98% purity) and Tokyo Chemical Industry Co.) was dissolved at 10% solids in Et-LGK at room temperature and formed a clear, uniform, yellow solution. After 24 hours at room temperature, there was no evidence of precipitation. Oxybenzone at 25% solids partially dissolved in Et-LGK at room temperature and completely dissolved with heating to 35-40° C. and formed a clear, uniform, yellow solution. Needle-shaped crystals formed over a 48-hour period at room temperature. Oxybenzone dissolved with heat at 20% solids in Et-LGK remained in solution after 24 hours of room temperature storage. Another solution prepared at 18% oxybenzone in Et-LGK showed no signs of precipitation after 5 days.

Oxybenzone was dissolved at 10% solids in Bu-LGK at room temperature. After 24 hours at room temperature, there was no evidence of precipitation.

Oxybenzone was dissolved at 40% solids in Et-LPK with heat and formed a clear, uniform, yellow solution. After 24 hours at room temperature, a precipitate formed. Oxybenzone was dissolved at 30% solids in Et-LPK with heat and formed a clear, uniform, yellow solution. After 24 hours at room temperature, there was no evidence of precipitation. The solution showed no signs of precipitation after 5 days.

Oxybenzone was dissolved at 28.5% solids in Et-LEK at room temperature. Oxybenzone was dissolved with heat at 37.5% solids in LEK. After 2 weeks at room temperature, there was no sign of precipitation.

Oxybenzone dissolved at room temperature in methyl-LGK to form clear solutions at the following concentrations: 1%, 1.8%, 2.9%, 4.3%, 6%, 7.6%, and 12.5%. Oxybenzone did not dissolve in methyl-LGK at room temperature at 14.9% solids.

Oxybenzone dissolved at room temperature in propyl-LGK to form clear solutions at the following concentrations: 1.5%, 2.75%, 4.9%, 7%, 9.4%, and 12.5%. Oxybenzone did not dissolve in propyl-LGK at room temperature at 17.8% solids.

Oxybenzone dissolved at room temperature in AcAc-GK to form clear solutions at the following concentrations: 1.9%, 5.3%, 9.7%, 13.9%, 17%, 20.6%, 23.9%, and 29%. Oxybenzone did not dissolve in ACAc-GK at room temperature at 31.9% solids.

Ethylhexyl methoxy cinnamate (octyl methoxycinnamate)

A 50/50 mixture of octyl methoxycinnamate (available from Spectrum Chemical) and Et-LGK was soluble at room temperature.

A 50/50 mixture of octyl methoxycinnamate and Bu-LGK was soluble at room temperature.

A 50/50 mixture of octyl methoxycinnamate and Et-LPK was soluble at room temperature.

The following Formulation Examples illustrate specific possible formulations for the manufacture of personal care formulations using the alkyl ketal esters of structure I. In particular, the alkyl ketal ester is methyl-LGK, ethyl-LGK, n-propyl-LGK, n-butyl-LGK, ethyl-LPK, n-butyl-LPK, ethyl-LEK, methyl-AcAcGK, ethyl-AcAcGK, ethyl-LTMEK, and ethyl-LTMPK. In a specific embodiment, the alkyl ketal ester is ethyl-LGK, ethyl-LPK, n-butyl-LGK, or a combination comprising at least one of the foregoing alkyl ketal esters.

Antiperspirant formulations are shown in Tables 22A-D.

TABLE 22A

| non-alcoholic deodorant stick | |
|---|---|
| Ingredient | weight % |
| Part A | |
| PPG-12 PEG-50 lanolin | 4 |
| Oleyl alcohol | 2 |
| Alkyl ketal ester* | 20 |
| Propylene glycol | 65.8 |
| Benzalkonium chloride | 0.2 |
| Part B | |
| Sodium stearate | 8 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the non-alcoholic deodorant stick, combine ingredients of Part A with mixing and heat to 70-80° C. Dust Part B into Part A with mixing. When uniform, cool to desired fill temperature.

TABLE 22B

| Water-in-oil (W/O) antiperspirant stick | |
|---|---|
| Ingredient | weight % |
| Part A | |
| Aluminum chlorohydrate (Microdry, Al. Chlorohydrate powder from Reheis Chemical Co.) | 19 |
| DI water | 25 |
| Part B | |
| Stearyl alcohol (CRODACOL S-95) | 25.5 |
| Polyglycerol oleate (EMCOL 14, Witco) | 5 |
| Sorbitan isostearate (SPAN 120, Croda) | 2.5 |

TABLE 22B-continued

Water-in-oil (W/O) antiperspirant stick

| Ingredient | weight % |
|---|---|
| Caprylic/capric triglyceride (CRODAMOL GTCC, Croda) | 6 |
| Alkyl ketal ester* | 6 |
| Cyclomethicone (Dow Corning 344 Fluid) | 9 |
| Dimethicone (Dow Corning 200 fluid, 350 cst) | 2 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the W/O antiperspirant, combine ingredients of Part A with mixing and heat to 75° C. until all aluminum chlorohydrate is dissolved. Combine ingredients of Part B with mixing and heat to 75° C. until uniform. Add Part A to Part B with rapid mixing while avoiding air entrapment. Allow to cool with mixing and pour into molds at 60-65° C.

TABLE 22C

Roll-on antiperspirant

| Ingredient | weight % |
|---|---|
| Part A | |
| Steareth-2 (VOLPO S-2, Croda) | 2.2 |
| Steareth-20 (VOLPO S-20, Croda) | 0.6 |
| PPG-10 cetyl ether | 5 |
| Ethanol | 5 |
| Alkyl ketal ester* | 5 |
| Part B | |
| DI water | 37.2 |
| Part C | |
| Aluminum chloride, 32 C Baum (Reheis Chemical Co.) | 5 |
| Chlorhydrol, 50% (Reheis Chemical Co.) | 40 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the roll-on antiperspirant, combine ingredients of Part A with mixing and heat to 65-70° C. Heat Part B to 65-70° C. Add Part B to Part A with mixing & cool to 45° C. Add Part C with mixing & cool to desired fill temperature.

TABLE 22D

24 Hour Antiperspirant/deodorant stick

| Ingredient | weight % |
|---|---|
| Part A | |
| PPG-11 stearyl ether | 5 |
| PPG-3 myristyl ether | 5 |
| Stearyl alcohol | 16.25 |
| Alkyl ketal ester* | 1.75 |
| Part B | |
| Cyclopentasiloxane and cyclohexasiloxane | 44.5 |
| Part C | |
| Silica dimethylsilylate | 3 |
| Aluminum chlorohydrate | 20 |
| Part D | |
| Polyglyceryl-3 caprylate | 0.5 |
| Zinc ricinoleate and lysine and propylene glycol | 4 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the AP/deodorant stick, melt Part A at 80-85° C. and stir until a clear paste forms. Cool Part A to 75-78° C. and add B to Part A while stirring. Stir for another 15 minutes. While stirring, add Part C to the batch Stir until C is homogeneously dispersed. Add Part D and stir for another 5 minutes. Compensate for the loss of B prior to filling. Fill while still warm.

TABLE 23

Lipstick.

| | Ingredient | weight % |
|---|---|---|
| Part A | Caprylic/Capric Triglyceride | 8.56 |
| | Octyldodecyl Stearoyl Stearate | 13.37 |
| | Triisostearyl Citrate | 4.05 |
| | Pentaerythrityl Tetraisostearate | 5.60 |
| | Jojoba Esters | 1.72 |
| | Lanolin Oil | 1.62 |
| | Bis-Diglyceryl Polyacyladipate-2 | 1.02 |
| | *Ricinus Communis* (Castor) Seed Oil | 20.50 |
| | *Copernicia Cerifera* (Carnauba) Wax | 2.30 |
| | *Euphorbia Cerifera* (Candelilla) Wax | 5.24 |
| | Cera Alba (Beeswax) | 2.09 |
| | Ozokerite Wax | 1.80 |
| | Microcrystalline Wax | 1.13 |
| | Phenoxyethanol | 1.00 |
| | Polyethylene | 1.00 |
| | Octyl Methoxycinnamate | 0.60 |
| | Tocopheryl Acetate | 0.05 |

TABLE 23-continued

Lipstick.

| | Ingredient | | weight % |
|---|---|---|---|
| Part B | *Ricinus Communis* (Castor) Seed Oil | | 10.00 |
| | D&C Red No. 6 Barium Lake | | 6.25 |
| | Iron Oxide | | 0.10 |
| | Alkyl ketal ester* | | 12 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, weigh Part A and begin heating to 80-85° C. with mixing. Pregrind Part B. When Part A is completely melted and clear, add Part B color grind to Part a wax/oil mixture. When all the color is dispersed and the batch is uniform, pour into molds.

TABLE 24

Solid Lip Gloss.

| | Ingredient | weight % |
|---|---|---|
| Part A | Castor oil | 36.4 |
| | Ketal* | 10 |
| | Polyisobutene 250 | 30 |
| | Bees wax | 10 |
| | Candelila wax | 9 |
| | Mica pigment | 3 |
| Part B | Vitamin E acetate | 1 |
| | BHT | 0.2 |
| | Food flavoring | 0.4 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, add Part A into a vessel and heat to 75° C. to melt wax, mixing until uniform. Remove from heat and add Part B, stirring well. While still liquid, pour into cosmetic container.

TABLE 25

Lip Balm.

| | Ingredient | weight % |
|---|---|---|
| Part A | Fractionated coconut oil | 13 |
| | Ketal | 10 |
| | Castor oil | 15 |
| | Triglyceride | 23 |
| | Shea butter | 12 |
| | Bees wax | 17 |
| | Lecithin | 1 |

TABLE 25-continued

Lip Balm.

| | Ingredient | weight % |
|---|---|---|
| Part B | Titanium dioxide (optional: nano-sized) | 2 |
| | Alkyl ketal ester* | 4.8 |
| Part C | Provitamin B5 | 1 |
| | Vitamin E acetate | 0.1 |
| | Vitamin E Tocopherol | 0.1 |
| | Allantoin | 0.2 |
| | Paraben-DU** | 0.5 |
| | Food flavoring | 0.3 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK
**Paraben-DU - premixed broad-spectrum preservative blend (3 wt. % propylparaben, 11 wt. % methylparaben, 30 wt. % diazolidinyl urea, 56 wt. % propylene glycol).

To manufacture the example formulations, pre-grind or pre-mix the ingredients of Part C. Add Part A to vessel and heat to 65 C until wax and butter are melted. Slowly add in Part C with mixing and mix until well dispersed. Remove from heat. Add ingredients of Part C to Parts A/B one by one and make sure the formulation is well mixed. Fill into molds while the formulation is still liquid. Allow to cool.

TABLE 26

Pressed Powder Eye Shadow "Nude Glitter"

| | Ingredient | weight % |
|---|---|---|
| Part A | Alkyl ketal ester* | 4 |
| | Cyclodimethicone | 3 |
| | Polyglyceryl oleate | 0.75 |
| | Vitamin E acetate | 1 |
| Part B | Pearl white mica | 31 |
| | Mica spheres (powder base) | 20 |
| | Talc powder (powder base) | 20 |
| | Beige mica | 5 |
| | Magnesium stearate | 5 |
| | Bismuth oxychloride (powder base) | 5 |
| | Titanium dioxide | 5 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, combine the titanium dioxide and the pearl white mica in a mortar, stir very well and thoroughly with the pestle until the color is uniform. Add then the other ingredients of Part B, one after another, mixing well after each addition. Then add Part A to the mortar and blend well, for several minutes or until the ingredients are mixed and the color looks uniform. Fill the eye shadow into an eye shadow jar and press it with a suitable tool into eye shadow containers.

TABLE 27

Poured Velvet Eyeshadow

| | Ingredient | weight % |
|---|---|---|
| Part A | Isostearyl neopentanoate | 25 |
| | Alkyl ketal ester* | 25 |
| | Isononyl isononanoate, polybutene, pentaerythrityl tetraisostearate, and isostearyl alcohol | 4 |
| | Ethylhexyl hydroxystearate, triethylhexyl trimellitates, and C30-45 olefin | 11 |
| Part B | Methyl methacrylate crosspolymer | 14 |
| Part C | CI 77491, mica, and triethoxycaprylylsilane | 20 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, heat Part A to 70 C until melted. Add Part B to Part A with stirring at 70° C. Add Part C to the combined Part A/B with stirring at 70° C. Pour into molds.

TABLE 28

Black Mascara.

| | Ingredient | weight % |
|---|---|---|
| Part A | Distilled Water | 68.4% |
| | Xanthan Gum | 0.2% |
| | Provitamin B5 | 0.5% |
| | Sorbitol or Glycerin | 2% |
| | Gum Arabic | 2% |
| Part B | Stearic Acid | 5% |
| | Candelilla Wax | 1.5% |
| | Ceteareth-20 | 1.7% |
| | Bees Wax | 4.5% |
| | Carnauba Wax | 2.7% |
| Part C | Iron Oxide Black | 10% |
| | Alkyl ketal ester* | 0.5% |
| Part D | Paraben-DU** | 1% |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK
**Paraben-DU - premixed broad-spectrum preservative blend (3 wt. % propylparaben, 11 wt. % methylparaben, 30 wt. % diazolidinyl urea, 56 wt. % propylene glycol).

To manufacture the example formulations, add Part A into a disinfected glass beaker and mix well until everything is dissolved. Add Part B into another disinfected glass beaker and heat to 75° C. Mix Part C well with mortar and pestle. When Part B is melted, add Part C and stir until the pigment is well dispersed. Heat Part A to the same temperature as Part B. Add the hot Part A slowly while stirring to hot Part B maintaining a temperature of 70° C. until the two ingredients are fully mixed. When the temperature has dropped below 60° C. add Part D and stir. While still hot and liquid fill into mascara containers by using a pipette.

TABLE 29

Anhydrous Mascara

| | Ingredient | weight % |
|---|---|---|
| Part A | Alkyl ketal ester* | 30.95 |
| | AC polyethylene 6a wax | 11 |
| | Candelilla wax | 4.5 |
| | Hydroxylated lanolin | 0.25 |
| Part B | pentaerythrityl rosinate | 2 |
| | C9-11 isoparaffin | 2 |
| Part C | methylparaben | 0.2 |
| | propylparaben | 0.1 |
| Part D | zinc stearate | 1 |
| Part E | silica silylate | 1 |
| Part F | Petroleum distillates, quaternium-18 hectorite, propylene carbonate | 35 |
| Part G | black iron oxide | 12 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, prepare Part B in advance by stirring in a sealed vessel until dissolved. In a separate closed vessel, combine the ingredients of Part A and heat to 90-95° C. with stirring. When Part A is clear and well-mixed, add Part B and Part C, stirring until dissolved. Add Parts D through F in sequential order, mixing well with high shear after each addition.

TABLE 30

Gel Eyeliner

| | Ingredient | weight % |
|---|---|---|
| Part A | Distilled Water | 70% |
| Part B | Alkyl Ketal Ester* | 7% |
| | Candelilla Wax | 5% |
| | Polyglucose | 1% |
| | Iron Oxide Black | 11% |
| | Microcrystalline Wax | 2% |
| | GelMaker EMU** | 3% |
| Part C | Phenoxyethanol-SA | 1% |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK
**Gelmaker EMU - pre-mixed gelling system (Sodium acrylate/acryloyldimethyl taurate copolymer/isohexadecane/polysorbate 80).

To manufacture the example formulations, add Part A into a heat resistant vessels and heat to 167° F. (75° C.). Add Part B to a heat resistant glass jar and heat to the same temperature. When Part B is fully melted add Part A to Part B, while stirring well. Remove from the heat but continue stirring until the mixture is a homogenous gel. If more thickness is needed, add more GelMaker EMU. Add Part C to Part A/B and stir again well. Package into small jars or into lip liner applicators by using a syringe

TABLE 31

Long Wearing Eyeliner/Eye Shadow Stick

| Ingredient | weight % |
|---|---|
| Carnauba wax | 4.5 |
| Ceresin | 12 |
| Ethyl hexyl palmitate | 6.5 |
| Alkyl ketal ester* | 5 |
| Polyglyceryl-3-diisostearate | 0.5 |
| Methylparaben | 0.2 |
| Propylparaben | 0.1 |
| Manganese violet | 5.5 |
| Ultramarine blue | 5.5 |
| Bismuth oxychloride | 20 |
| Silica silylate | 1 |
| Cyclomethicone | 39.2 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, combine the waxes and oils in a sealed high speed mixer. Heat to 85-90° C. until waxes are dissolved. Add pigments. Agitate until no undispersed pigments remain. Fill at 70-75° C. using hermetically sealed equipment.

TABLE 32

Colored Pencil

| | Ingredient | weight % |
|---|---|---|
| Part A | Ethyl cellulose | 1.5 |
| | Isostearyl alcohol | 5.9 |
| | Stearyl alcohol | 5.9 |
| Part B | Hydrogenated vegetable oil | 6.7 |
| | Paraffin | 6.7 |
| Part C | Colorants | 33.3 |
| | Alkyl ketal ester* | 5 |
| Part D | Cyclomethicone | 35 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, mix Part A and heat at 65-90° C. with stirring until everything dissolves. Maintain temperature of Part A. In a separate vessel, mix Part B and melt. Add molten Part B to hot Part A. Mix Part C and add to Parts A/B. Homogenize mixture and then mix in Part D. Pour mixture into a mold to cool. Remove the pencil from mold when solidified and cooled.

TABLE 33

Cream Blush

| | Ingredient | Weight % |
|---|---|---|
| Part A | Triglyceride (emollient) | 22.8% |
| | Alkyl ketal ester* | 15% |
| | Meadowfoam seed oil (emollient) | 10% |
| | Shea butter (emollient) | 3% |
| | Polyglyceryl oleate (emulsifier) | 2% |
| | Stearyl palmitate (thickener) | 3% |
| | Carnauba wax (thickener) | 2% |
| | Vitamin E tocopherol (antioxidant) | 0.2% |
| Part B | Kaolin (texturizer) | 7% |
| | Corn Starch AS (texturizer) | 10% |
| | Mica Spheres (texturizer) | 12% |
| | Pearl white Mica (color) | 4% |
| Part C | Mica Red (color) | 8% |
| | Phenoxyethanol/SA (preservative) | 1% |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, add Part A into a disinfected glass beaker and heat to 176° F./80° C. to melt the ingredients. Add Part B to Part A and stir well. Then add Part C to Part A/B and stir again well. Remove from the heat and pour into a compact case or small pot containers and let cool. Color can be adjusted through the pigment choice and level. Consistency can be adjusted by changing stearyl palmitate and ketal levels.

TABLE 34

Powder Cream Blush

| | Ingredient | weight % |
|---|---|---|
| Part A | PPG-3 benzyl ether myristate | 38 |
| | Tribehenin | 6 |
| | C18-36 acid triglyceride | 1 |
| | Sorbitan isostearate | 1 |
| | Methyl paraben | 0.2 |
| | Propyl paraben | 0.1 |
| Part B | D&C Red #6 Lake | 0.1 |
| | D&C Red #7 Lake | 0.1 |
| | AS 5126 Red Iron oxide color techniques | 0.9 |
| | AS 5146 Black Iron oxide color techniques | 0.2 |
| | Alkyl ketal ester* | 2 |
| Part C | AS Duan Talc 50707 Color techniques | 20.4 |
| | Mica AS Sericite 5061 Color techniques | 14 |
| | Bismuth oxychloride | 16 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, add part A to vessel and heat at 75-80° C. with stirring until clear. In a separate vessel, blend part B and pass over a 3 roll-mill until particle size is 20 micrometers. Add Part B to Part A and stir until smooth and pigments are wetted. Maintain temperature at 75-80° C. Add Part C and mix at high speed until homogeneous. Allow to de-air while hot and then pour into pans.

TABLE 35

Oil in Water Foundation

| | Ingredient | weight % | Function |
|---|---|---|---|
| Part A | DI water | 50.92 | Diluents |
| | tromethamine | 0.8 | alkali (soap) |
| | PEG-12 dimethicone | 0.1 | wetting agent |
| | 80% TiO2/talc extender | 8 | Pigment |
| | 80% yellow iron oxide/talc ext. | 0.95 | Pigment |
| | 80% red iron oxide/talc ext | 0.75 | Pigment |
| | 80% black iron oxide/talc ext. | 0.07 | Pigment |
| | talc, average 4 micron | 4.23 | Filler |
| Part B | butylene glycol | 4 | Humectants |
| | magnesium aluminum silicate | 1 | Thickener |
| Part C | butylene glycol | 2 | Humectants |
| | cellulose gum | 0.15 | Thickener |
| Part D | sucrose cocate | 1 | Emulsifier |
| | methyl paraben | 0.2 | Preservative |
| | disodium EDTA | 0.05 | preservative aid |
| Part E | stearic acid | 1.5 | acid portion of soap |
| | isostearic acid | 0.5 | Soap |
| | dicaprylyl maleate | 10 | Emollient |
| | Alkyl ketal ester* | 6 | Emollient |
| | sorbitol monolaurate | 3 | Emulsifier |
| | cetyl alcohol | 0.5 | Stabilizer |
| | propyl paraben | 1 | Preservative |
| Part F | cyclomethicone | 2 | volatile emollient |
| Part G | DI water | 2 | Diluents |
| | DMDM hydantoin | 0.1 | Preservative |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, combine Part A ingredients in order while homogenizing. Combine and add Part B. Heat to 85-90° C. for 15 minutes and then cool to 75° C. Combine and add Part C. Add Part D ingredients in order. Combine ingredients of Part E and heat to 75-80° C. with stirring. Just prior to emulsification, add Part F and readjust temperature to 75-80° C. Add oil phase (combined Parts E and F) to water phase (combined Parts A-D) while homogenizing. Maintain temperature and agitation for at least 15 minutes. Cool to 55° C. and check for water loss. Cool to 45° C. with paddle mixer. Combine ingredients of Part G and add to the formulation. Cool to 30° C. and remove from heat.

TABLE 36

Foundation

| | Ingredient | weight % |
|---|---|---|
| Part A | DI water | 50 |
| | Potassium hydroxide (10% aq. solution) | 1.3 |
| | Polysorbate 80 | 0.1 |
| | Alkyl ketal ester* | 4.33 |

TABLE 36-continued

Foundation

| | Ingredient | weight % |
|---|---|---|
| Part B | Titanium dioxide | 7 |
| | Talc | 3.76 |
| | Yellow iron oxide | 0.8 |
| | Red iron oxide | 0.36 |
| | Black iron oxide | 0.09 |
| Part C | Propylene glycol | 2 |
| | Magnesium aluminum silicate | 1 |
| Part D | Propylene glycol | 4 |
| | Cellulose gum | 0.12 |
| Part E | Di-ppg-3 Myristyl ether adipate | 12 |
| | Alkyl ketal ester* | 4 |
| | Cetearyl alcohol, ceteth-20 phosphate, dicetyl phosphate | 3 |
| | Steareth-10 | 2 |
| | Cetyl alcohol | 0.62 |
| | Steareth-2 | 0.50 |
| Part F | Paraben-DU** | 1 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK
**Paraben-DU - premixed broad-spectrum preservative blend (3 wt. % propylparaben, 11 wt. % methylparaben, 30 wt. % diazolidinyl urea, 56 wt. % propylene glycol).

To manufacture the example formulations, combine Part A and begin homogenizing. Pre-mill Part B until pigments are well blended. Add Part B to Part A and homogenize until pigments are evenly dispersed. Begin heating A/B. Prepare a slurry of Part C and add to Parts A/B and heat to 85° C., maintaining temperature in the 85-90° C. range for 10 minutes. Remove from heat and prepare a second slurry of the ingredients in Part D. Add the slurried of Part D to A/B/C at 77° C. Homogenize until uniform and smooth. Check weight and add water to compensate for any loss, plus another 20 g/kg of formulation. Continue mixing and increase temperature to 77 C. Combine Part E ingredients separately and heat to 77° C. Add to main mixture and maintain temperature at 77-80° C. for 10 minutes. Remove from heat. Add Part F when the mixture has cooled to 50° C. Check for water loss and adjust formulation accordingly. Adjust pH to 7.5 if necessary. Homogenize until temperature reaches 35° C.

In a variation, one of the alkyl ketal esters is a blend of Et-LGK and an alkyl ketal ester of Exs. B-K.

TABLE 37

Concealer Stick

| | Ingredient | weight % |
|---|---|---|
| Part A | Titanium dioxide (A-8112) | 20 |
| | Red iron oxide (A-1301) | 1.4 |
| | Red Iron Oxide (A-1226) | 0.65 |
| | Black iron oxide (A-7133) | 0.1 |
| | Alkyl ketal ester* | 15.85 |
| | Di-PPG-3 Myristyl Ether Adipate | 4.25 |
| | Sorbitan Isostearate | 4.25 |
| Part B | Sericite AS | 10 |
| | Talc | 5 |
| | Di-PPG-3 Myristyl ether adipate | 2.5 |
| | Kaolin | 4 |

TABLE 37-continued

Concealer Stick

| | Ingredient | weight % |
|---|---|---|
| Part C | Squalane | 3.5 |
| | Candelilla wax | 5 |
| | Ozokerite wax | 2.5 |
| | Propyl paraben | 0.1 |
| | Methyl paraben | 0.2 |
| | Carnauba wax | 1.75 |
| | C18-36 acid glycol ester | 2.25 |
| | C18-36 Acid Triglyceride | 1.1 |
| | Di-PPG-3 Myristyl ether Adipate | 14.6 |
| | DERMAXYL (from Croda) | 1 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, grind the ingredients of Part A and homogenize for at least 15 minutes. Add the ingredients of Part B to Part A and mix for at least 10 minutes. Combine all of the ingredients of Part C in a separate vessel and begin heating while mixing. Continue heating until batch becomes clear. Begin cooling while mixing and add Parts A/B to the batch. Pre-warm the stick molds and pour the batch into molds while the batch is still pourable. Allow molds to cool.

TABLE 38

Pressed Mineral Powder

| | Ingredient | weight % |
|---|---|---|
| Part A | Pigment blend (color of choice) | 3 |
| | Titanium dioxide | 3 |
| | Talc | 26 |
| | Bismuth oxychloride | 15 |
| | Magnesium stearate | 12 |
| | Micronized titanium dioxide | 6 |
| | Kaolin | 5.5 |
| | Zinc oxide | 2 |
| Part B | Alkyl ketal ester* | 3.5 |
| | Grapeseed oil | 2 |
| | Triglycerides | 2 |
| Part C | Mica spheres | 20 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, mill Part A until it turns a uniform color. Add part B to Part A and mill again. Add Part C and blend for only a short time. Fill container and compress to form a solid.

TABLE 39

Loose Mineral Powder

| | Ingredient | weight % |
|---|---|---|
| Part A | Pigment blend (color of choice) | 3 |
| | Titanium dioxide | 5 |
| | Talc | 26 |
| | Bismuth oxychloride | 15 |
| | Magnesium stearate | 12 |
| | Micronized titanium dioxide | 7 |
| | Kaolin | 5.5 |
| | Zinc oxide | 3 |
| Part B | Alkyl ketal ester* | 3.5 |
| Part C | Mica spheres | 20 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, mill Part A until it turns a uniform color. Add part B to Part A and mill again. Add Part C and blend for only a short time. Fill container. Do not compress.

TABLE 40

Baby Soft Diaper Rash Cream

| | Ingredient | weight % |
|---|---|---|
| Part A | Squalane | 30 |
| | Alkyl Ketal Ester* | 5 |
| | Zinc oxide | 12 |
| | CRODAFOS CES (cetearyl alcohol, dicetyl phosphate, and ceteth-10 phosphate) | 6 |
| Part B | Deionized water | 44.10 |
| | Methylparaben, butylparaben, ethylparaben, and propylparaben | 0.3 |
| Part C | Dimethicone | 0.6 |

*Alkyl ketal ester examples:
Ex. A, methyl-LGK
Ex. B, ethyl-LGK
Ex. C, n-propyl-LGK
Ex. D, n-butyl-LGK
Ex. E, ethyl-LPK
Ex. F, n-butyl-LPK
Ex. G, ethyl-LEK
Ex. H, Me-AcAcGK
Ex. I, Et-AcAcGK
Ex. J, ethyl-LTMEK
Ex. K, ethyl-LTMPK To manufacture the example formulations, disperse zinc oxide in the ketal and then add the other ingredients of Part A individually with mixing. Heat to 70-75° C. In a separate vessel, combine Part B and heat to 70-75° C. Add Part B to Part A and mix well. Begin cooling and add Part C with mixing when temperature reaches 50° C. Continue mixing and cool to desired fill temperature.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The endpoints of all ranges directed to the same component or property are inclusive of the endpoint and independently combinable.

Unless otherwise defined, all terms (including technical and scientific terms) used herein have the same meaning as commonly understood by one of ordinary skill in the art to which this invention belongs.

The above-described compounds have, in embodiments, one or more isomers. Where an isomer can exist, it should be understood that the invention embodies methods that form any isomer thereof, including any stereoisomer, any conformational isomer, and any cis, trans isomer; isolated isomers thereof; and mixtures thereof.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. Alkyl groups may be straight-chained or branched. Hydroxyl groups have the formula —OH.

As used herein, a "formulation" refers to both a composition that can be used to manufacture a product, and the product itself, i.e., in the form provided to the user. Compositions can be used to manufacture a product by addition of one or more additional ingredients and/or subjecting the formulation to one or more processing steps, including in some embodiments simply packaging the composition.

As used herein, a "low VOC" formulation or product contains no more than 60 wt. % by weight of components that contain at least one carbon atom and meets all of the following conditions: (A) has vapor pressure more than 0.1 mm Hg at 20° C., as determined by ARB Method 310; (B) contains less than 12 carbon atoms, and (C) has a boiling point less than 216° C., as determined by ARB Method 310.

Further as used herein, unless indicated otherwise by context, an "alcohol" means a C1-7 alkanol such as methanol, ethanol, 1-propanol, 2-propanol, 1-butanol, 2-butanol, t-butanol, 1-pentanol, and 1-hexanol, as well as the various other isomers of pentanol and hexanol; alkylene glycols such as ethylene glycol, diethylene glycol, triethylene glycol, 1,2-propylene glycol, 1,3-propane diol, dipropylene glycol, tripropylene glycol 1,4-butane diol and 1,2-butane diol; triols such as glycerine, and the like. In an embodiment, an alcohol is methanol, ethanol, 1-propanol, 2-propanol, 1-butanol, 2-butanol, t-butanol, 1-pentanol, 1-hexanol, ethylene glycol, 1,2-propylene glycol, and 1,3-propane diol.

All cited patents, patent applications, and other references are incorporated herein by reference in their entirety.

The various embodiments described above are provided by way of illustration only and should not be construed to limit the claims attached hereto. The present invention can suitably comprise, consist of, or consist essentially of, any of the disclosed or recited elements. Thus, the invention illustratively disclosed herein can be suitably practiced in the absence of any element, which is not specifically disclosed herein. Various modifications and changes will be recognized that can be made without following the example embodiments and applications illustrated and described herein, and without departing from the true spirit and scope of the following claims.

What is claimed is:

1. A personal care formulation comprising an alkyl ketal ester, wherein the alkyl ketal ester is methyl levulinate propylene glycol ketal (methyl-LPK), ethyl levulinate propylene glycol ketal (ethyl-LPK), and n-butyl levulinate propylene glycol ketal (n-butyl LPK), or a combination comprising at least one of the foregoing; and an active agent selected from organic anti-aging agents, organic anti-acne agents, organic skin whiteners, organic ultraviolet light absorbers, organic tanning agents, organic anti-alopecia agents, antifungal agents, anti-dandruff active agents, anti-perspirant active agents, antimicrobial agents, organic medicinals, depilatory compounds, hair dyes, organic insect repellants, and a combination thereof;

wherein methyl-LPK is of the formula:

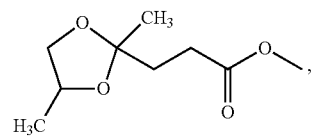

ethyl-LPK is of the formula:

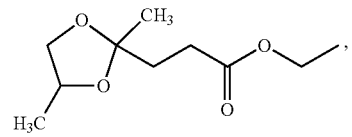

n-butyl-LPK is of the formula:

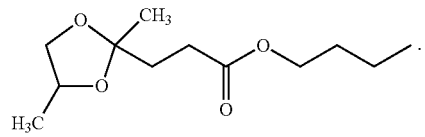

2. The formulation of claim 1, wherein the active agent is lactic acid, 2-hydroxydecanoic acid, 2-hydroxyoctanoic acid and glycolic acid, beta-hydroxy acids such as beta-hydroxy salicylic acid, avobenzone, benzoate-4-methylbenzylidene, cinoxate, dioxybenzone, homosalate, menthyl anthranilate, mexoryl SX, drometrizole trisiloxane, octocrylene, octyl methoxycinnamate, ethylhexyl salicylate, oxybenzone, padimate O, p-aminobenzoic acid (PABA), phenylbenzimidazole sulfonic acid, sulisobenzone, titanium trolamine salicylate, salicylic acid, a retinoic acid, benzoyl peroxide, hydroquinone, arbutun, a plant extract containing arbuten, kojic acid, azelaic acid, glycyrrhetic acid, levulinic acid, 2-cyano-3,3-diphenylacrylic acid, sodium benzotriazolyl butylphenol sulfonate, ethyl-2-cyan-3,3-diphenylacrylate, 2-t-butyl-6-(5-chloro-2H-benzotriazol-2-yl)-p-cresol, 2-(2-H-benzotriazol-2-yl)-4-methylphenol, benzophenone-12, bornelone, 2-benzotriazolyl-4-tert-octylphenol, dihydroxyacetone, erythrulose, dihydroxyacetone-ortho-ethyl acetate, canthaxanthin, afamelanotide, minoxidil, finasteride, dutasteride, ketoconazole, zinc pyrithione, selenium sulfide, clotrimazole, tea tree oil, piroctone olamine, an amphetamine, an antihistamine, methylphenidate, oxymetazoline, tetrahydrolzoline hydrochloride, psilocybin calcium, thioglycolate, sodium thioglycolate, thioglycolic acid, ammonium thioglycolate, butyl thioglycolate, ethanolamine thioglycolate, glyceryl thioglycolate, isooctyl thioglycolate, isopropyl thioglycolate, magnesium thioglycolate, methyl thioglycolate, potassium thioglycolate, aluminum zirconium tetrachlorohydrex gly, aluminum chlorohydrate, aluminum chloride, resorcinol, 1-napthol, p-aminophenol, p-phenylenediamine, salts of p-phenylenediamine, 4-amino-2-hydroxytoluene, phenoxyethanol, N,N-diethyl-m-toluamide, p-menthane-3,8-diol, nepetalactone, citronella oil, permethrin, neem oil, bog myrtle extract, or a combination comprising at least one of the foregoing active agents.

3. The formulation of claim 1, comprising from 0.001 to 40% by weight of the active agent, based on the total weight of the personal care formulation.

4. The formulation of claim 2, comprising from 0.001 to 30% by weight of the active agent and from 2 to 60% by weight of water, each based on the total weight of the personal care formulation.

5. The formulation of claim 1, further comprising at least one of
(a) a paraffinic, naphthenic, or aromatic mineral oil,
(b) a nonionic organic compound having
a melting temperature of less than 45° C.,
a molecular weight of at least 190 Daltons,
an amido or ester group, and
an alkyl chain containing at least 8 carbon atoms, and
a solubility in water of no greater than 1 part in 99 parts of water;
(c) a nonionic organosilicone compound having
a melting temperature of less than 45° C., and
a solubility in water of no greater than 1 part in 99 parts of water;
(d) a long chain alcohol; and
(e) a wax.

6. The formulation of claim 1, further comprising at least one fully water miscible alkyl ketal ester.

7. The formulation of claim 1, further comprising at least one partially water-miscible alkyl ketal ester.

8. The formulation of claim 1, comprising at least one sparingly water-miscible alkyl ketal ester.

9. The formulation of claim 1, comprising water and a partially- or fully water-miscible alkyl ketal ester which together form a cosolvent mixture into which at least one active is dissolved.

10. The formulation of claim 1, comprising an alcoholic phase or an alcohol-water phase, and an alkyl ketal ester that is miscible in the alcohol to the extent of at least 10 parts of the alkyl ketal ester in 90 parts by weight of the alcohol, wherein the alkyl ketal ester and at least one active agent is at least partially dissolved into the alcoholic phase or alcohol-water phase.

11. The formulation of claim 9, wherein the alcohol is ethanol, isopropanol, 1,2-propylene glycol, or 1,3-propane diol.

12. The formulation of claim 1, in the form of an emulsion comprising an aqueous phase and an oil phase, wherein the aqueous phase comprises the alkyl ketal ester, and the alkyl ketal ester is partially or fully water-miscible.

13. The formulation of claim 1, in the form of an emulsion comprising an aqueous phase and an oil phase, wherein the oil phase comprises the alkyl ketal ester.

14. The formulation of claim 1, wherein the alkyl ketal ester is ethyl-LPK, n-butyl-LPK or a combination comprising at least one of the foregoing alkyl ketal esters.

15. The formulation of claim 1, further comprising at least one fragrance.

16. The formulation of claim 1, further comprising at least one surfactant.

17. The formulation of claim 1, further comprising nitrocellulose, modified corn starch, acrylates/octylacrylamide copolymer, polyurethane-14 and AMP-acrylates copolymer, hydrolyzed wheat protein, polyvinylpyridine, hydrolyzed wheat protein/PVP crosspolymer, vinyl acetate/crotonates/vinyl neodecanoate copolymers, potassium butyl ester of PVM/MA copolymer, polyurethane-14 and AMP-acrylates copolymer, isobutylene/ethyl maleimide/hydroxylethylmaleimide copolymer, polyvinylpyrrolidine/vinyl acetate polymers, acrylates/hydroxyesters acrylates copolymer, polyurethanes, polyvinyl methyl ester/maleate, octylacrylamide/acrylates/butylaminoethyl methacrylate copolymer, or a combination comprising at least one of the foregoing polymers.

18. A waxy personal care formulation comprising
a wax,
an emollient, and
an alkyl ketal ester, wherein the alkyl ketal ester is methyl levulinate propylene glycol ketal (methyl-LPK), ethyl levulinate propylene glycol ketal (ethyl-LPK), and n-butyl levulinate propylene glycol ketal (n-butyl LPK), or a combination comprising at least one of the foregoing;
wherein methyl-LPK is of the formula:

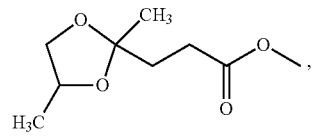

ethyl-LPK is of the formula:

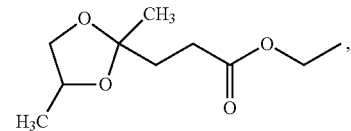

n-butyl-LPK is of the formula:

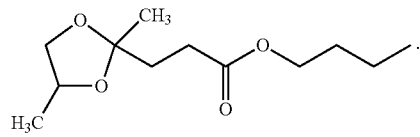 [SMILES: CCCCOC(=O)CCC1(C)OCC(C)O1 ; "."]

19. The formulation of claim 18, further comprising from 0.5 to 10% by weight of a polar compound, based on the total weight of the formulation.

20. The formulation of claim 19, wherein the polar compound is water.

21. The formulation of claim 18, wherein the alkyl ketal ester is ethyl-LPK, n-butyl-LPK or a combination comprising at least one of the foregoing alkyl ketal esters.

22. A personal care formulation in the form of an emulsion, comprising
i) a continuous phase and a disperse phase wherein the continuous phase or the disperse phase is an aqueous phase and the other is an oil phase; or at least two co-continuous phases wherein at least one of the co-continuous phases is an aqueous phase and at least one of the co-continuous phases is an oil phase; and wherein any of the foregoing oil phases comprises at least one of
(a) a paraffinic, naphthenic, or aromatic mineral oil,
(b) a nonionic organic compound having
   a melting temperature of less than 45° C.,
   a molecular weight of at least 190 Daltons,
   an amido or ester group, and
   an alkyl chain containing at least 8 carbon atoms, and
   a solubility in water of no greater than 1 part in 99 parts of water,
(c) a nonionic organosilicone compound having
   a melting temperature of less than 45° C., and
   a solubility in water of no greater than 1 part in 99 parts of water,
(d) a long chain alcohol, and
(e) a wax; and
ii) an alkyl ketal ester, wherein the alkyl ketal ester is methyl (methyl-LPK), ethyl levulinate propylene glycol ketal (ethyl-LPK), and n-butyl levulinate propylene glycol ketal (n-butyl LPK), or a combination comprising at least one of the foregoing;
wherein methyl-LPK is of the formula:

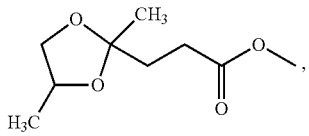

ethyl-LPK is of the formula:

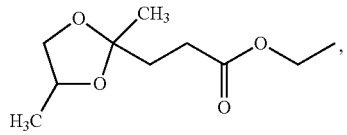

n-butyl-LPK is of the formula:

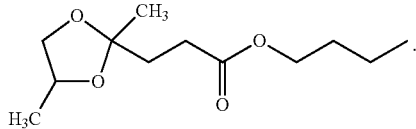

23. The formulation of claim 22, wherein the alkyl ketal ester is a partially or fully water-miscible alkyl ester located at least partially in the aqueous phase.

24. The formulation of claim 22, wherein the alkyl ketal ester is ethyl-LPK, n-butyl-LPK, or a combination comprising at least one of the foregoing.

25. The formulation of claim 24, wherein the alkyl ketal ester is at least partially located in the oil phase.

26. A personal care formulation comprising
an alkyl ketal ester, wherein the alkyl ketal ester is methyl levulinate propylene glycol ketal (methyl-LPK), ethyl levulinate propylene glycol ketal (ethyl-LPK), and n-butyl levulinate propylene glycol ketal (n-butyl LPK), or a combination comprising at least one of the foregoing; and
an additional cosmetically acceptable ingredient;
wherein methyl-LPK is of the formula:

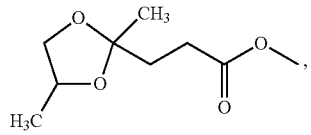

ethyl-LPK is of the formula:

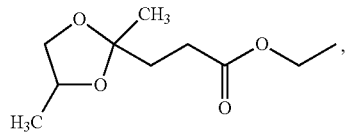

n-butyl-LPK is of the formula:

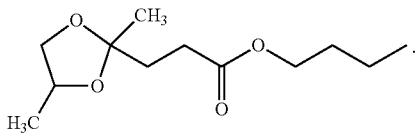

27. The formulation of claim 26, in the form of a solution, dispersion, emulsion, gel, ointment, or solid.

28. The formulation of claim 26, comprising an aqueous phase, an alcohol phase, or an alcohol/water phase in which at least a portion of the alkyl ketal ester is dissolved.

29. The formulation of claim 26 which is an emulsion that contains at least one aqueous phase and at least one oil phase, and the alkyl ketal ester is in the aqueous phase, the oil phase, both the aqueous and oil phases, or at the interface between the aqueous and oil phases.

30. The formulation of claim 26, which is a solution that contains water and an alkyl ketal ester dissolved in the water, and wherein at least one of said cosmetically acceptable ingredients is immiscible in water but is dissolved in the water/alkyl ketal ester mixture.

31. The formulation of claim 26, wherein the alkyl ketal ester is selected from ethyl-LPK, n-butyl-LPK, and combinations thereof.

* * * * *